US008318897B2

(12) United States Patent
Birkenmeyer et al.

(10) Patent No.: US 8,318,897 B2
(45) Date of Patent: Nov. 27, 2012

(54) **NUCLEOTIDE AND AMINO ACID SEQUENCES ENCODING AN EXPORTED PROTEIN 1 DERIVED FROM *PLASMODIUM VIVAX* AND USES THEREOF**

(75) Inventors: Larry G. Birkenmeyer, Glenview, IL (US); Ruthie E. Coffey, Hawthrone Woods, IL (US); George J. Dawson, Libertyville, IL (US); Suresh M. Desai, Libertyville, IL (US); Bruce J. Dille, Antioch, IL (US); Anthony Scott Muerhoff, Kenosha, WI (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 13/219,802

(22) Filed: Aug. 29, 2011

(65) Prior Publication Data

US 2011/0311572 A1    Dec. 22, 2011

Related U.S. Application Data

(62) Division of application No. 12/412,529, filed on Mar. 27, 2009, now Pat. No. 8,063,193.

(51) Int. Cl.
*G01N 33/531* (2006.01)
*C07K 14/445* (2006.01)
*A61K 39/002* (2006.01)

(52) U.S. Cl. .................... 530/324; 435/7.1; 424/191.1
(58) Field of Classification Search .................. None
See application file for complete search history.

(56) References Cited

U.S. PATENT DOCUMENTS

| | | | |
|---|---|---|---|
| 4,582,788 | A | 4/1986 | Erlich |
| 4,683,194 | A | 7/1987 | Saiki et al. |
| 4,683,202 | A | 7/1987 | Mullis |
| 4,948,882 | A | 8/1990 | Ruth |
| 5,006,309 | A | 4/1991 | Khalil et al. |
| 5,063,081 | A | 11/1991 | Cozzette et al. |
| 5,089,424 | A | 2/1992 | Khalil et al. |
| 5,107,065 | A | 4/1992 | Shewmaker et al. |
| 5,231,020 | A | 7/1993 | Jorgensen et al. |
| 5,424,414 | A | 6/1995 | Mattingly |
| 5,464,746 | A | 11/1995 | Fino |
| 5,700,671 | A | 12/1997 | Prieto et al. |
| 5,705,330 | A | 1/1998 | Shah et al. |
| 5,750,176 | A | 5/1998 | Prieto et al. |
| 6,248,329 | B1 * | 6/2001 | Chandrashekar et al. . 424/191.1 |
| 6,395,472 | B1 | 5/2002 | Leary et al. |
| 2003/0170881 | A1 | 9/2003 | Davis et al. |
| 2004/0018577 | A1 | 1/2004 | Emerson Campbell et al. |
| 2005/0054078 | A1 | 3/2005 | Miller et al. |
| 2006/0160164 | A1 | 7/2006 | Miller et al. |

FOREIGN PATENT DOCUMENTS

| | | | |
|---|---|---|---|
| EP | 50424 | B1 | 9/1985 |
| EP | 84796 | B1 | 5/1990 |
| EP | 237362 | B1 | 3/1992 |
| EP | 201184 | B1 | 12/1992 |
| EP | 258017 | B1 | 6/1997 |
| WO | WO9220702 | A1 | 11/1992 |

OTHER PUBLICATIONS

Hill (Phil. Trans. R. Soc. B, 366:2806-2814, 2011).*
Ellis (Chapter 29 of Vaccines, Plotkin, et al. (eds) WB Saunders, Philadelphia, 1998, 568-575.*
Bowie et al. (Science, 1990, 247:1306-1310).*
Greenspan et al. (Nature Biotechnology 7: 936-937, 1999).*
Son et al. (Korean J. Parasitol., 39:171-176, 2001).*
http://www.ncbi.nlm.nih.gov/nucleotide/9890/, accessed Mar. 7, 2012.*
Ausubel F.M., et al., eds., Current Protocols in Molecular Biology, vol. 1, John Wiley & Sons Inc., 2004, Table of Contents.
Boerner P., et al., "Production of Antigen-Specific Human Monoclonal Antibodies from in Vitro-Primed Human Splenocytes," Journal of Immunology, 1991, vol. 147 (1), pp. 86-95.
Brennan M., et al., "Preparation of Bispecific Antibodies by Chemical Recombination of Monoclonal Immunoglobulin G1 Fragments," Science, 1985, vol. 229, pp. 81-83.
Carlton J.M., et al., "Comparative Genomics of the Neglected Human Malaria Parasite *Plasmodium vivax*," Nature, 2008, vol. 455 (7214), pp. 757-763.
Carter P., "Site-Directed Mutagenesis," Biochemical Journal, 1986, vol. 237 (1), pp. 1-7.
Charoenvit Y., et al., "CD4(+) T-cell- and Gamma Interferon-Dependent Protection against Murine Malaria by Immunization with Linear Synthetic Peptides from a *Plasmodium yoelii* 17-Kilodalton Hepatocyte Erythrocyte Protein," Infection and Immunity, 1999, vol. 67 (11), pp. 5604-5614.
Circumsporozoite-protein related antigen, XP002583503, 2009.
Doderer C., et al., "A new ELISA kit which uses a Combination of *Plasmodium falciparum* Extract and Recombinant *Plasmodium vivax* Antigens as an Alternative to IFAT for Detection of Malaria Antibodies," Malaria Journal, 2007, vol. 6, pp. 19.
Doolan D.L., et al., "Identification and Characterization of the Protective Hepatocyte Erythrocyte Protein 17 kDa Gene of *Plasmodium yoelii*, Homolog of *Plasmodium falciparum* Exported Protein 1," The Journal of Biological Chemistry, 1996, vol. 271 (30), pp. 17861-17868.
Elghouzzi M. H., et al., "Multicentric Evaluation of the DiaMed enzyme-Linked Immunosorbent Assay Malaria Antibody test for Screening of Blood Donors for Malaria," Vox Sanguinis, 2008, vol. 94 (1), pp. 33-40.
EMBL, "*Plasmodium vivax* ctg_6977, Whole Genome Shotgun Sequence," Accession No. AAKM01000005; AAKM01000000; AAKM00000000, XP002583502.

(Continued)

*Primary Examiner* — Nita M Minnifield
*Assistant Examiner* — Brian J Gangle
(74) *Attorney, Agent, or Firm* — Cheryl L. Becker

(57) ABSTRACT

The present invention is directed to novel polynucleotides and polypeptides directed to EXP1 of *Plasmodium vivax*, and methods of using these polynucleotides and polypeptides in the detection of *P. vivax* antibodies or anti-*P. vivax* antibodies in a subject. The invention finds particular useful application in identifying recent exposure to *P. vivax*.

16 Claims, 2 Drawing Sheets

OTHER PUBLICATIONS

Fishwild D.M., et al., "High-Avidity Human IgG Kappa Monoclonal Antibodies from a Novel Strain of Minilocus Transgenic Mice," Nature Biotechnology, 1996, vol. 14 (7), pp. 845-51.

Galfre G., et al., "Antibodies to Major Histocompatibility Antigens Produced by Hybrid Cell Lines," Nature, 1977, vol. 266 (5602), pp. 550-552.

Girard M.P., et al., "A review of Human Vaccine Research and Development: Malaria," Vaccine, 2007, vol. 25 (9), pp. 1567-80.

Goding J. W., "Monoclonal antibodies: Principles and Practice", 1996, Academic Press, pp. 492.

Harlow E., et al., Antibodies: A Laboratory Manual, Cold Spring Harbor Laboratory Press, 1988, pp. 555-561, 578-582 and 591-592.

Holliger P., et al., ""Diabodies": Small Bivalent and Bispecific Antibody Fragments," Proceedings of the National Academy of Sciences of the USA, 1993, vol. 90 (14), pp. 6444-6448.

Hoogenboom H.R., et al., "Multi-Subunit Proteins on the Surface of Filamentous Phage: Methodologies for Displaying Antibody (Fab) Heavy and Light Chains," Nucleic Acids Research, 1991, vol. 19 (15), pp. 4133-4137.

Hope I.A., et al., "Evidence for Immunological Cross-Reaction between Sporozoites and Blood stages of a Human Malaria Parasite," Nature, 1984, vol. 308 (5955), pp. 191-194.

Ingelbrecht I.L., et al., "Different 3' End Regions Strongly Influence the Level of Gene Expression in Plant Cells," The Plant Cell, 1989, vol. 1 (7), pp. 671-680.

International Search Report for Application No. PCT/US2010/028234, mailed on Jun. 21, 2010, 5 pages.

Invitrogen (Product Catalog. 1997).

Jones J.D., et al., "High Level Expression of Introduced Chimaeric Genes in Regenerated Transformed Plants," The EMBO Journal, 1985, vol. 4 (10), pp. 2411-2418.

Jones P.T., et al., "Replacing the Complementarity-Determining Regions in a Human Antibody with those from a Mouse," Nature, 1986, vol. 321 (6069), pp. 522-525.

Kara U., et al., "Chemical Characterization of the Parasitophorous Vacuole Membrane Antigen QF 116 from Plasmodium falciparum," Molecular and Biochemical Parasitology, 1990, vol. 38 (1), pp. 19-23.

Kaufman R.J., "Vectors Used for Expression in Mammalian Cells," Methods in Enzymology, 1990, vol. 185, pp. 487-511.

Kim S., et al., "ELISA Detection of Vivax Malaria with Recombinant Multiple stage-Specific Antigens and its Application to Survey of Residents in Endemic Areas," Korean Journal of Parasitology, 2003, vol. 41 (4), pp. 203-207.

Kim S., et al. "ELISA-based detection of vivax malaria using recombinant 6xHis-tagged antigens," Qiagen, 2005, vol. 1, pp. 1-32.

Kitchen A.D., et al., "Evaluation of a Malarial Antibody Assay for use in the Screening of Blood and Tissue Products for Clinical use," Vox Sanguinis, 2004, vol. 87 (3), pp. 150-155.

Kostelny S.A., et al., "Formation of a Bispecific Antibody by the Use of Leucine Zippers," Journal of Immunology, 1992, vol. 148 (5), pp. 1547-1553.

Lee J.S., et al., "Current Status of Vivax Malaria among Civilians in Korea," Korean Journal of Parasitology, 1998, vol. 36 (4), pp. 241-248.

Lonberg N., et al., "Antigen-Specific Human Antibodies From Mice Comprising Four Distinct Genetic Modifications," Nature, 1994, vol. 368, pp. 856-859.

Lonberg N., et al., "Human Antibodies from Transgenic Mice," International Reviews of Immunology, 1995, vol. 13 (1), pp. 65-93.

Luckow V. A., "Cloning and expression of heterologous genes in insect cells with baculovirus vectors in Recombinant DNA technology and applications," 1991, A. Prokop, R.K. Bajpai, and C. Ho, editors. McGraw-Hill, pp. 97-152.

Marks J.D., et al., "By-passing Immunization. Human Antibodies from V-gene Libraries Displayed on Phage," Journal of Molecular Biology, 1991, vol. 222 (3), pp. 581-597.

Marks J.D., et al., "By-Passing Immunization: Building High Affinity Human Antibodies by Chain Shuffling," Biotechnology, 1992, vol. 10 (7), pp. 779-783.

Meraldi V., et al., "Natural Antibody Response to Plasmodium falciparum Exp-1, Msp-3 and Glurp Long Synthetic Peptides and Association with Protection," Parasite Immunology, 2004, vol. 26 (6-7), pp. 265-272.

Meraldi V., et al., "Recognition of Synthetic Polypeptides Corresponding to the N- and C-terminal Fragments of Plasmodium falciparum Exp-1 by T-Cells and Plasma from Human donors from African Endemic Areas," Parasite Immunology, 2002, vol. 24 (3), pp. 141-150.

Mertens G., et al., "Malaria Antibody ELISA Insufficiently Sensitive for Blood Donor Screening," Vox Sanguinis, 1999, vol. 77 (4), pp. 237-238.

Milstein C., et al, "Hybrid Hybridomas and their use in Immunohistochemistry," Nature, 1983, vol. 305 (5934), pp. 537-540.

Morrison S.L., et al., "Genetically Engineered Antibody Molecules and their Application," Annals of the New York Academy of Sciences, 1987, vol. 507, pp. 187-198.

Mullis K., et al., "Specific Enzymatic Amplification of DNA in Vitro: The Polymerase Chain Reaction," Cold Spring Harbor Symposia on Quantitative Biology, 1986, vol. 51 (Pt 1), pp. 263-273.

Mungai M" " et al "Transfusion-Transmitted Malaria in the United States from 1963 through 1999," New England Journal of Medicine, 2001, vol. 344 (26), pp. 1973-1978.

Munson P.J., et al., "Ligand: A Versatile Computerized Approach for Characterization of Ligand-Binding Systems," Analytical Biochemistry, 1980, vol. 107 (1), pp. 220-39.

Nielsen P.E., et al., "Sequence-selective Recognition of DNA by Strand Displacement with a Thymine-substituted Polyamide," Science (New York, N.Y.), 1991, vol. 254 (5037), pp. 1497-1500.

Okamuro J.K., et al., "Regulation of Plant Gene Expression: General Principles" in: The Biochemistry of Plants: A Comprehensive Treatise, vol. 15, Marcus A., ed., Academic Press Limited, 1989, pp. 1-82.

Reisfeld R.A., et al., eds., Monoclonal Antibodies and Cancer Therapy: Proceedings of the Roche-UCLA Symposium, Alan R. Liss, Inc., 1985, Table of Contents.

Riechmann L., et al., "Reshaping Human Antibodies for Therapy," Nature, 1988, vol. 332 (6162), pp. 323-327.

Rodrigues M.H., et al., "Serological Detection of Plasmodium vivax Malaria Using Recombinant Proteins Corresponding to the 19-Kda C-Terminal Region oftThe Merozoite Surface Protein-1," Malaria Journal, 2003, vol. 2 (1), pp. 39.

Sambrook J., et al., "Molecular Cloning: A Laboratory Manual," 1989, 2nd Ed., Cold Spring Harbor Laboratory Press, Table of Contents.

Schade R., et al., "The Production of Avian (Egg Yolk) Antibodies: IgY," ATLA, 1996, vol. 24, pp. 925-34.

Schnieke A.E., et al., "Human Factor IX Transgenic Sheep Produced by Transfer of Nuclei from Transfected Fetal Fibroblasts," Science, 1997, vol. 278 (5346), pp. 2130-2133.

Seed C.R., et al., "The Efficacy of a Malarial Antibody Enzyme Immunoassay for Establishing the Reinstatement Status of Blood Donors Potentially Exposed to Malaria," Vox Sanguinis, 2005, vol. 88 (2), pp. 98-106.

Shah et al., "PRISM antigen and antibody assays," The Immunoassay Handbook, 2001, 2nd Ed., David Wild, ed., pp. 297-303.

Shalaby M.R., et al., "Development of Humanized Bispecific Antibodies Reactive with Cytotoxic Lymphocytes and Tumor Cells Overexpressing the HER2 Protooncogene," The Journal of Experimental Medicine, 1992, vol. 175, pp. 217-225.

She R.C., et al., "Comparison of Immunofluorescence Antibody Testing and two Enzyme Immunoassays in the Serologic Diagnosis of Malaria," Journal of Travel Medicine, 2007, vol. 14 (2), pp. 105-111.

Sherman I.W., "Membrane Structure and Function of Malaria Parasites and the Infected Erythrocyte," Parasitology, 1985, vol. 91 (Pt 3), pp. 609-645.

Simmons D., et al., "A Malaria Protein Exported into a new Compartment within the Host Erythrocyte," EMBO Journal, 1987, vol. 6 (2), pp. 485-491.

Son E.S., et al., "Western Blot Diagnosis of Vivax Malaria with Multiple Stage-Specific Antigens of the Parasite," Korean Journal of Parasitology, 2001, vol. 39 (2), pp. 171-176.

Srivastava I.K., et al., "Comparative Evaluation of an ELISA based on Recombinant Polypeptides and IFA for Serology of Malaria," Journal of Tropical Medicine and Hygiene, 1991, vol. 94 (3), pp. 189-194.

Suresh M.R., et al., "Bispecific Monoclonal Antibodies from Hybrid Hybridomas in: Production of Hybridomas," Methods in Enzymology, 1986, vol. 121, pp. 210-228.

Tolle R., et al., "A Prospective Study of the Association between the Human Humoral Immune Response to *Plasmodium falciparum* Blood stage Antigen gp190 and Control of Malarial Infections," Infection and Immunity, 1993, vol. 61 (1), pp. 40-47.

Traunecker A., et al., "Myeloma Based Expression System for Production of Large Mammalian Proteins," Trends in Biotechnology, 1991, vol. 9 (4), pp. 109-13.

Turner R., et al., "The Potential Exploitation of Plant Viral Translational Enhancers in Biotechnology for Increased Gene Expression," Molecular Biotechnology, 1995, vol. 3(3), pp. 225-236.

Urlaub G., et al., "Isolation of Chinese Hamster Cell Mutants Deficient in Dihydrofolate Reductase Activity," Proceedings of the National Academy of Sciences of the USA, 1980, vol. 77 (7), pp. 4216-4220.

Van Der Krol A.R., et al., "Modulation of Eukaryotic Gene Expression by Complementary RNA or DNA Sequences," BioTechniques, 1988, vol. 6 (10), pp. 958-976.

Verhoeyen M., et al., "Reshaping Human Antibodies: Grafting an Antilysozyme Activity," Science, 1988, vol. 239, pp. 1534-1536.

Vinetz J.M., et al., "*Plasmodium malariae* Infection in an Asymptomatic 74-year-old Greek woman with Splenomegaly," New England Journal of Medicine, 1998, vol. 338 (6), pp. 367-371.

Wells J.A., et al., "Cassette Mutagenesis: an Efficient Method for Generation of Multiple Mutations at defined Sites," Gene, 1985, vol. 34 (2-3), pp. 315-323.

Wild D., The Immunoassay Handbook, 2001, Nature Pub. Group, Table of Contents.

Written Opinion for Application No. PCT/US2010/028234, mailed on Jun. 21, 2010, 8 pages.

Wyler D., "*Plasmodium* and *Babesia*," in: Infectious Diseases, 1992, S.L. Gorbach, J.G. Bartlett, and N. R. Blacklow, eds., pp. 1967-1978.

Zoller M.J., et al., "Oligonucleotide-Directed Mutagenesis: a simple Method using two Oligonucleotide Primers and a Single-Stranded DNA Template," Methods in Enzymology, 1987, vol. 154, pp. 329-350.

Zon G., "Oligonucleotide Analogues as Potential Chemotherapeutic Agents," Pharmaceutical Research, 1988, vol. 5 (9), pp. 539-549.

* cited by examiner

GAATTCCATGAACGCCGGTAACGGTCGTCATCCATTTTCTCTGGGTGGTGGTAAAGG

TGGCGACGCGGCGCCTACGGAGCCGACGCCGGCACCGACCGCGCCGAGCGCAACTG

GTCTGAACGATGACGGTTCTTCTTCTGGCACTGAATCTACTTCTCATCATCACCATCA

CCATTGAGGATCC

Figure 1B

MNAGNGRHPFSLGGGKGGDAAPTEPTPAPTAPSATGLNDDGSSSGTESTSHHHHHH

Figure 1C

Bio-NAGNGRHPFSLGGGKGGDAAPTEPTPAPTAPSATGLNDDGSSSGTESTS

A Prototype Abbott PRISM® Malaria Assay Format

Step 1

Transfer Wash

Step 2

Wash, Activate and Read

| | | | |
|---|---|---|---|
|  | Recombinant PvEXP1 coated microparticle |  | Acridinium labeled mouse anti-human IgG |
|  | Human sample with anti-plasmodium antibodies | SD | Specimen diluent buffer |

SEQUENCE LISTING

```
<160> NUMBER OF SEQ ID NOS: 4

<210> SEQ ID NO 1
<211> LENGTH: 184
<212> TYPE: DNA
<213> ORGANISM: Plasmodium vivax
<220> FEATURE:
<221> NAME/KEY: CDS
<222> LOCATION: (8)..(175)

<400> SEQUENCE: 1 gaattcc atg aac gcc ggt aac ggt cgt cat cca ttt tct ctg ggt ggt       49
        Met Asn Ala Gly Asn Gly Arg His Pro Phe Ser Leu Gly Gly
        1               5                   10 ggt aaa ggt ggc gac gcg gcg cct acg gag ccg acg ccg gca ccg acc       97
Gly Lys Gly Gly Asp Ala Ala Pro Thr Glu Pro Thr Pro Ala Pro Thr
15                  20                  25                  30 gcg ccg agc gca act ggt ctg aac gat gac ggt tct tct tct ggc act      145
Ala Pro Ser Ala Thr Gly Leu Asn Asp Asp Gly Ser Ser Ser Gly Thr
                35                  40                  45 gaa tct act tct cat cat cac cat cac cat tgaggatcc                    184
Glu Ser Thr Ser His His His His His His
            50                  55

<210> SEQ ID NO 2
<211> LENGTH: 56
<212> TYPE: PRT
<213> ORGANISM: Plasmodium vivax

<400> SEQUENCE: 2

Met Asn Ala Gly Asn Gly Arg His Pro Phe Ser Leu Gly Gly Gly Lys
1               5                   10                  15

Gly Gly Asp Ala Ala Pro Thr Glu Pro Thr Pro Ala Pro Thr Ala Pro
            20                  25                  30

Ser Ala Thr Gly Leu Asn Asp Asp Gly Ser Ser Ser Gly Thr Glu Ser
        35                  40                  45
```

```
Thr Ser His His His His His His
    50                  55

<210> SEQ ID NO 3
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asn Ala Gly Asn Gly Arg His Pro Phe Ser Leu Gly Gly Gly Lys Gly
1               5                   10                  15

Gly Asp Ala Ala Pro Thr Glu Pro Thr Pro Ala Pro Thr Ala Pro Ser
            20                  25                  30

Ala Thr Gly Leu Asn Asp Asp Gly Ser Ser Ser Gly Thr Glu Ser Thr
        35                  40                  45

Ser

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 4

His His His His His His
1               5
```

NUCLEOTIDE AND AMINO ACID SEQUENCES ENCODING AN EXPORTED PROTEIN 1 DERIVED FROM *PLASMODIUM VIVAX* AND USES THEREOF

CROSS-REFERENCE TO RELATED APPLICATIONS

The present application is a divisional of allowed U.S. patent application Ser. No. 12/412,529, hereby incorporated in its entirety by reference.

FIELD

The subject invention relates to nucleic acid sequences and amino acid sequences encoded thereby, derived from the Exported Antigen-1 (EXP1) gene of *Plasmodium vivax*, useful in diagnostic applications, among others.

BACKGROUND

Malaria Transmittance

Malaria is a mosquito-borne disease caused by a parasite. At least four species of malaria parasites can infect humans under natural conditions: *Plasmodium falciparum, P. vivax, P. ovale* and *P. malariae*. The first two species cause the most infections worldwide. *P. vivax* and *P. ovale* have dormant liver stage parasites (hypnozoites) that can reactivate (or "relapse") and cause malaria several months or years after the infecting mosquito bite; consequently, these species can be difficult to detect in infected individuals.

In nature, malaria parasites spread by infecting successively two types of hosts: humans and female *Anopheles* mosquitoes. In humans, the parasites grow and multiply first in the liver cells and then in the red blood cells. In the blood, successive broods of parasites grow inside the red cells and destroy them, releasing daughter parasites (merozoites) that continue the cycle by invading other red cells.

The blood stage parasites cause the symptoms of malaria. When certain forms of blood stage parasites, gametocytes, are picked up by a female *Anopheles* mosquito during a blood meal, they start another, different cycle of growth and multiplication in the mosquito. After 10-18 days, the parasites are found as sporozoites in the mosquito's salivary glands. When the *Anopheles* mosquito takes a blood meal from another human, the sporozoites are injected with the mosquito's saliva and start another human infection when they parasitize the liver cells (Wyler, 1992).

Malaria Symptoms and Disease

Infection with malaria parasites can result in a wide variety of symptoms, ranging from absent or very mild symptoms to severe disease and even death. Malaria disease can be categorized as uncomplicated or (complicated) severe. In general, malaria is curable if diagnosed and treated promptly. Following the infective mosquito bite there is an incubation period before the first symptoms appear. The incubation period usually varies from 7 to 30 days. The shorter periods are observed most frequently with *P. falciparum* and the longer with *P. vivax*. In fact, *P. vivax* can have extended incubation periods, over 450 days (Lee et al., 1998).

Diagnosis

Malaria must be recognized promptly in order to treat the patient in time and to prevent further spread of infection in the community. Because of the long incubation period for *P. vivax*, diagnosis can be difficult by traditional blood smear methods, delaying treatment. Delay in diagnosis and treatment is a leading cause of death in malaria patients. Malaria can be suspected based on a patient's symptoms and physical findings at examination. However, for a definitive diagnosis, laboratory tests must demonstrate presence of the malaria parasites. The present diagnostic "gold standard" for malaria depends on the demonstration of parasites on a blood smear examined under a microscope.

Detection of *Plasmodium* Antibodies

Antibodies to asexual malaria parasites (i.e., merozoites) appear within days to weeks after the parasites invade erythrocytes and can persist for months or even years (Vinetz et al., 1998). Antibody detection for diagnosis of acute malaria is usually not recommended, however, because the presence of antibodies can indicate past or recent infection. Enzyme-linked immunosorbent assays (ELISA) have been developed that use *Plasmodium*-derived antigens (Newmarket Laboratories, UK; Cellabs, Australia) or *P. falciparum* whole organism lysates (DiaMed) to detect immunoglobulins (IgG and/or IgM) in human serum or plasma. These assays are easier to perform, exhibit higher throughput and better sensitivity and specificity than IFA (Kitchen et al., 2004; Seed et al., 2005; Srivastava et al., 1991). Current commercial ELISA assays are insufficiently sensitive to detect antibodies directed against each of the four plasmodium species (She et al., 2007).

Antigens used to capture antibodies have included vaccine candidates. These antigens are attractive for diagnostic applications because these antigens are known to elicit antibody responses, and thus are likely to be useful to detecting antibodies produced by infected individuals that result from parasite infection. Examples of such antigens include circumsporozoite protein (CSP), apical membrane antigen 1 (AMA-1), merozoite surface protein (MSP) one and two, of both *P. vivax* and *P. falciparum* (Kitchen et al., 2004; Rodrigues et al., 2003). Other antigens of interest are MSP-2, -3, -4, -5, -8 -9, glutamate-rich protein, and serine repeat antigen (Girard et al., 2007).

Exported Protein-1 (EXP1; also known as QF116, antigen 5.1, and circumsporozoite related antigen (Meraldi et al., 2002)) has been studied in *Plasmodium* sp., although its ortholog in *P. vivax* has not been elucidated except by sequence gazing. In non-*P. vivax* species, the polypeptide is a vesicular protein that is thought to be important in intracellular transport of parasite proteins (Simmons et al., 1987). In *P. falciparum*, EXP1 is expressed as a 23 kD protein in the pre-erythrocytic and asexual blood stages of the parasite (Hope et al., 1984). An integral membrane protein, it is found in the membranes of parasitophorous vacuoles (endoplasmic and reticulum enshrouded vacuoles that protect intracellular parasites) and in vesicles within the host cell cytoplasm (Kara et al., 1990; Sherman, 1985; Tolle et al., 1993). Studies using an EXP1 murine homolog showed that the protein can induce protective T-cell immunity in mice against lethal challenges with *P. yoelii* (Charoenvit et al., 1999). Antibodies raised against *P. falciparum* EXP1 polypeptides have been successful in detecting malaria infections (Meraldi et al., 2002). Generally, the C-terminus is most antigenic in humans (Meraldi et al., 2002).

There have been reports of using *P. vivax* EXP1 sequences as tools to diagnose *P. vivax* infection (Kim et al., 2003; Son et al., 2001); however, these early efforts appear to have been based on incorrect sequences and the resulting diagnostics most likely detected *P. falciparum* EXP1 sequences. In both the Kim et al. (2003) and Son et al. (2001) reports, the authors used primer sequences apparently developed using the sequences disclosed by Simmons et al. (Simmons et al., 1987). Simmons et al. (1987) reported on *P. falciparum* EXP1 sequences, and noted that the sequence was highly conserved in five *P. falciparum* lines; however, Simmons et al. (1987) did not report on any EXP1 sequences from *P. vivax*. Kim et al. (2003) and Son et al. (2001) cite GenBank Accession No. X05074 as being from *P. vivax*; however, GenBank's entry indicates that this accession is part of *P. falciparum*. To circumvent this, Kim et al. (2003) and Son et al. (2001) used for a template blood from a *vivax* malaria patient, but data analysis suggests that the primers they used would not amplify *P. vivax* polynucleotide sequences because the last 3 nucleotides (3') of the forward primer, and the last 6 nucleotides (3') of the reverse primer do not anneal to the putative *P. vivax* EXP1 sequence as understood today.

Detection of antibodies in donated serum or plasma can be used to identify individual donors who have been exposed to malarial organisms and who may be recently infected and, therefore, potentially parasitemic. All four species of plasmodium that infect humans have been transmitted via blood transfusion, and though the incidence of post-transfusion malaria is low in the United States (Mungai et al., 2001), the availability of blood donors could be increased by implementation of plasmodium antibody screening assays such that only malaria-organism exposed individuals are deferred from blood donation rather than all donors who have traveled or lived in malaria endemic regions, as is the current practice. Such assays would theoretically detect antibodies against plasmodium species that infect humans and cause malaria (*P. falciparum, P. vivax, P. ovale,* and *P. malariae*). Commercial antibody ELISAs are currently in use (United Kingdom, Australia, France) or are being considered in other countries for the reinstatement of deferred donors (Elghouzzi et al., 2008; Kitchen et al., 2004; Seed et al., 2005). In these cases, donors are tested for antibodies to plasmodium derived antigens within several months of deferral.

A commercial assay (Pan Malaria Antibody CELISA) from Cellabs Pty. Ltd. (Brookvale, NSW, Australia) claims detection of antibodies to all four plasmodium species that cause malaria in humans and sensitivity of 94% versus immunofluoresence test (IFAT) (per package insert). Independent evaluation suggests the assay has poor sensitivity for *falciparum* and non-*falciparum* malaria antibody detection when compared to IFAT (Mertens et al., 1999). Independent evaluation of another assay from DiaMed AG (Switzerland) which utilizes a mixture of extracts of cultured *P. falciparum* and *P. vivax* recombinant protein (circumsporozoite protein), demonstrated poor sensitivity for detection of symptomatic individuals with microscopically confirmed *P. vivax* (18/24) but did detect antibodies in patients infected with *P. ovale* (2/2), or *P. malariae* (2/2) infection (Doderer et al., 2007). The malaria antibody assay manufactured by Newmarket Laboratories Ltd (Kentford, UK) claims detection of all four species of plasmodium responsible for human malaria though it contains only *P. falciparum* and *P. vivax* derived recombinant antigens. The package insert indicates sensitivity for *P. ovale* and *P. malariae* antibody detection of only 80% and 67%, respectively. Detection of antibodies among individuals infected with *P. ovale* or *P. malariae* may be due to past infection with either *P. falciparum* or *P. vivax* and hence reactivity is due to detection of persistent antibodies to these agents. Independent evaluation of the assay demonstrated detection of only 9/14 (64%) of patients with acute malaria due to *P. ovale* infection and 85% (15/18) of patients with *P. vivax* malaria (Kitchen et al., 2004). Hence, the claimed ability of these assays to detect human antibodies elicited by infection to *P. falciparum* as well as *P. ovale, P. vivax* and *P. malariae* is questionable. For those assays whose composition of solid phase antigen is known (e.g. Newmarket, DiaMed), the absence of *P. ovale* or *P. malariae* specific antigens suggests that detection of antibodies to these species may be due to antibody cross-reactivity which raises important questions about assay specificity as well as sensitivity, or the reactivity observed in *P. ovale* or *P. malariae* samples is due to the presence of *P. falciparum* or *P. vivax* antibodies from previous infections.

Thus, there is presently a significant need for reliable detection of plasmodium antibodies from *P. vivax*.

All patents and publications referred to herein are hereby incorporated in their entirety by reference.

SUMMARY

In a first aspect, the invention is directed to isolated nucleic acid sequences or fragments thereof comprising or complementary to a nucleic acid sequence encoding a polypeptide, wherein the amino acid sequence of said polypeptide has at least 70% identity to an amino acid sequence selected from the group consisting of SEQ ID NO:2, SEQ ID NO:3 and amino acids 2-50 of SEQ ID NO:2. The nucleic acid sequence can be, for example, that of SEQ ID NO:1, or isolated from *Plasmodium vivax*.

In a second aspect, the invention is directed to purified proteins encoded by a nucleic acid having at least 70% sequence identity with the nucleic acid sequence of SEQ ID NO:1.

In a third aspect, the invention is directed to purified proteins or fragments thereof comprising an amino acid sequence having at least 70% identity to an amino acid sequence selected from the group consisting of SEQ ID NO:2, SEQ ID NO:3, and amino acids 2-50 of SEQ ID NO:2.

In a fourth aspect, the invention is directed to methods of producing a protein, wherein the method comprises the steps of:

(a) isolating a nucleic acid sequence comprising the nucleotide sequence of SEQ ID NO:1;

(b) constructing a vector comprising the isolated nucleic acid sequence operably linked to a regulatory sequence; and (c) introducing said vector into a host cell for a time and under conditions sufficient for expression of said protein.

The host cell can be a prokaryotic or eukaryotic cell.

In a fifth aspect, the invention is directed to vectors comprising a nucleic acid sequence comprising SEQ ID NO:1, operably linked to a regulatory sequence, and to host cells comprising such vectors.

In a sixth aspect, the invention is directed to methods of detecting antibodies to *P. vivax* in a test sample suspected of containing the antibodies comprising the steps of:

(a) contacting the test sample with an antigen comprising an amino acid sequence selected from the group consisting of SEQ ID NO:2, SEQ ID NO:3, and amino acids 2-50 of SEQ ID NO:2, for a time and under conditions sufficient for the formation of antibody/antigen complexes; and (b) detecting the presence of antibodies present in the test sample by detecting presence of the antibody/antigen complexes.

In a seventh aspect, the invention is directed to methods of detecting antibodies to *P. vivax* in a test sample suspected of containing the antibodies comprising the steps of:

(a) contacting the test sample with an antigen comprising an amino acid sequence selected from the group consisting of SEQ ID NO:2, SEQ ID NO:3, and amino acids 2-50 of SEQ ID NO:2, for a time and under conditions sufficient to allow for the formation of antibody/antigen complexes;

(b) adding a conjugate to resulting antibody/antigen complexes for a time and under conditions sufficient to allow the conjugate to bind to bound antibody, wherein the conjugate comprises an antibody attached to a signal generating compound capable of generating a detectable signal; and (c) detecting the presence of antibodies present in the test sample by detecting presence of the signal generated by the signal generating compound.

In an eighth aspect, the invention is directed to methods of detecting antibodies to *P. vivax* in a test sample suspected of containing the antibodies comprising the steps of:

(a) contacting the test sample with an antigen comprising an amino acid sequence selected from the group consisting of SEQ ID NO:2, SEQ ID NO:3, and amino acids 2-50 of SEQ ID NO:2, for a time and under conditions sufficient to allow for the formation of antibody/antigen complexes;

(b) adding a conjugate to resulting antibody/antigen complexes for a time and under conditions sufficient to allow the conjugate to bind to bound antibody, wherein the conjugate comprises an antigen comprising an amino acid sequence selected from the group consisting of SEQ ID NO:2, SEQ ID NO:3, and amino acids 2-50 of SEQ ID NO:2, attached to a signal generating compound capable of generating a detectable signal; and (c) detecting the presence of antibodies present in the test sample by detecting presence of the signal generated by the signal generating compound In a ninth aspect, the invention is directed to methods of detecting the presence of *P. vivax* antibodies in a test sample suspected of containing the antibodies comprising the steps of:

(a) contacting the test sample with anti-antibody for a time and under conditions sufficient to allow for formation of anti-antibody/*P. vivax* antibody complexes;

(b) adding antigen to the resulting anti-antibody/*P. vivax* antibody complexes for a time and under conditions sufficient to allow the antigen to bind to bound antibody, wherein the antigen comprises an amino acid sequence selected from the group consisting of SEQ ID NO:2, SEQ ID NO:3, and amino acids 2-50 of SEQ ID NO:2;

(c) adding a conjugate to the resulting anti-antibody/*P. vivax* antibody/antigen complexes, wherein the conjugate comprises a composition comprising a monoclonal or polyclonal antibody raised against *P. vivax* antibody/antigen complexes attached to a signal generating compound capable of generating a detectable signal; and (d) detecting the presence of antibodies which can be present in the test sample by detecting presence of the signal generated by the signal generating compound.

In yet a tenth aspect, the invention is directed to methods of detecting antibodies to *P. malariae, P. falciparum, P. vivax* and *P. ovale* in a test sample suspected of containing at least one of the antibodies comprising the steps of:

(a) contacting the test sample with: (i) an antigen comprising an amino acid sequence selected from the group consisting of SEQ ID NO:2, SEQ ID NO:3, and amino acids 2-50 of SEQ ID NO:2, (ii) an antigen from *P. falciparum*; (iii) an antigen from *P. ovale*, and (iv) an antigen from *P. malariae*, for a time and under conditions sufficient for the formation of *P. malariae* antibody/antigen complexes, *P. falciparum* antibody/antigen complexes, *P. vivax* antibody/antigen complexes and *P. ovale* antibody/antigen complexes; and (b) detecting the presence of antibodies present in the test sample by detecting presence of one or more of the complexes.

In an eleventh aspect, the invention is directed to methods of detecting antibodies to *P. malariae, P. ovale, P. vivax* and *P. falciparum* in a test sample suspected of containing at least one of the antibodies comprising the steps of:

(a) contacting the test sample with: (i) an antigen comprising an amino acid sequence selected from the group consisting of SEQ ID NO:2, SEQ ID NO:3, and amino acids 2-50 of SEQ ID NO:2, (ii) a *P. ovale* antigen, (iii) a *P. malariae* antigen and (iv) a *P. falciparum* antigen, for a time and under conditions sufficient to allow for the formation of *P. malariae* antibody/antigen complexes, *P. ovale* antibody/antigen complexes, *P. vivax* antibody/antigen complexes and *P. falciparum* antibody/antigen complexes;

(b) adding four conjugates to the resulting antibody/antigen complexes for a time and under conditions sufficient to allow each conjugate to bind to bound antibody, wherein a first conjugate comprises an antigen comprising an amino acid sequence selected from the group consisting of SEQ ID NO:2, SEQ ID NO:3, and amino acids 2-50 of SEQ ID NO:2, attached to a signal generating compound capable of generating a detectable signal; a second conjugate comprises a *P. ovale* antigen attached to a signal generating compound capable of generating a detectable signal; a third conjugate comprises a *P. malariae* antigen attached to a signal generating signal capable of generating a detectable signal and a fourth conjugate comprises a *P. falciparum* antigen attached to a signal generating compound capable of generating a detectable signal; and (c) detecting the presence of antibody to *P. malariae, P. ovale, P. vivax* and *P. falciparum* which can be present in the test sample by detecting presence of the signal generated by the signal generating compound.

In a twelfth aspect, the invention is directed to methods of detecting antibodies to *P. malariae, P. ovale, P. vivax* and *P. falciparum* in a test sample suspected of containing at least one of the antibodies comprising the steps of:

(a) contacting the test sample with (i) an antigen comprising an amino acid sequence selected from the group consisting of SEQ ID NO:2, SEQ ID NO:3, and amino acids 2-50 of SEQ ID NO:2, (ii) *P. malariae* antigen, (iii) a *P. vivax* antigen and (iv) a *P. falciparum* antigen, for a time and under conditions sufficient to allow for the formation of *P. malariae* antibody/antigen complexes, *P. ovale* antibody/antigen complexes, *P. vivax* antibody/antigen complexes and *P. falciparum* antibody/antigen complexes;

(b) adding a conjugate to the resulting antibody/antigen complexes for a time and under conditions sufficient to allow each conjugate to bind to bound antibody, wherein the conjugate comprises an antibody attached to a signal generating compound capable of generating a detectable signal; and (c) detecting the presence of antibody to *P. malariae, P. ovale, P. vivax* and *P. falciparum* antibody which can be present in the test sample by detecting presence of the signal generated by the signal generating compound.

In a thirteenth aspect, the invention is directed to methods for detecting the presence of antibodies to *P. malariae, P. ovale, P. vivax* and *P. falciparum* in a test sample suspected of containing at least one of the antibodies comprising the steps of:

(a) contacting the test sample with anti-antibody for a time and under conditions sufficient to allow for formation of anti-antibody/*P. vivax*, anti-antibody/*P. malariae*, anti-antibody/*P. ovale*, and anti-antibody/*P. falciparum* complexes;

(b) adding a first antigen, a second antigen, a third antigen, and a fourth antigen to the resulting anti-antibody/*P. vivax*, anti-antibody/*P. malariae*, anti-antibody/*P. ovale*, and anti-antibody/*P. falciparum* complexes for a time and under conditions sufficient to allow the antigens to bind to bound antibody, wherein (i) the first antigen comprises an amino acid sequence selected from the group consisting of SEQ ID NO:2, SEQ ID NO:3, and amino acids 2-50 of SEQ ID NO:2;

(ii) the second antigen comprises a *P. ovale* antigen; (iii) the third antigen comprises a *P. malariae* antigen; and (iv) the fourth antigen comprises a *P. falciparum* antigen;

(c) adding a first conjugate, a second conjugate, a third conjugate and a fourth conjugate to the resulting anti-antibody/antibody/antigen complexes for a time and under conditions sufficient to allow the conjugates to bind to bound antibody, wherein the conjugates are each attached to a signal generating compound capable of generating a detectable signal; and (i) the first conjugate comprises a composition comprising a monoclonal or polyclonal antibody raised against *P. vivax* antibody/antigen complexes; (ii) the second conjugate comprises a composition comprising a monoclonal or polyclonal antibody raised against *P. ovale* antibody/antigen complexes; (iii) the third conjugate comprises a composition comprising a monoclonal or polyclonal antibody raised against *P. malariae* antibody/antigen complexes; (vi) the fourth conjugate comprises a composition comprising a monoclonal or polyclonal antibody raised against *P. falciparum* antibody/antigen complexes; and (d) detecting presence of antibodies which can be present in the test sample by detecting presence of the signal generated by the signal generating compounds.

In a fourteenth aspect, the invention is directed to methods for detecting the presence of antibodies to *P. malariae, P. ovale, P. vivax* and *P. falciparum* in a test sample suspected of containing at least one of the antibodies comprising the steps of:

(a) contacting the test sample with anti-antibody to allow for the formation of anti-antibody/antibody complexes;

(b) adding a first conjugate, a second conjugate, a third conjugate and a fourth conjugate to resulting anti-antibody/antibody complexes for a time and under conditions sufficient to allow the conjugates to bind to bound antibody, wherein the first conjugate comprises an antigen comprising an amino acid sequence selected from the group consisting of SEQ ID NO:2, SEQ ID NO:3, and amino acids 2-50 of SEQ ID NO:2, attached to a signal generating compound capable of generating a detectable signal, wherein the second conjugate comprises a *P. ovale* antigen attached to a signal generating compound capable of generating a detectable signal, wherein the third conjugate comprises a *P. vivax* antigen attached to a signal generating compound capable of generating a detectable signal, and wherein the fourth conjugate comprises a *P. falciparum* antigen attached to a signal generating compound capable of generating a detectable signal; and (c) detecting the presence of antibodies to *P. malariae, P. ovale, P. vivax* and *P. falciparum* in the test sample by detecting presence of the signal generated by the signal generating compound.

In a fifteenth aspect, the invention is direct to vaccines comprising: (a) at least one antigen selected from the group consisting of: (i) an antigen comprising an amino acid sequence of SEQ ID NO:2, SEQ ID NO:3, and amino acids 2-50 of SEQ ID NO:2, or an epitope thereof. Such vaccines can further comprise an antigen selected from the group consisting of *P. falciparum, P. ovale*, and *P. malariae*; and a pharmaceutically acceptable adjuvant.

In a sixteenth aspect, the invention is directed to kits for determining the presence of antibody to *P. vivax* in a test sample comprising: (a) an antigen comprising an amino acid sequence selected from the group consisting of SEQ ID NO:2, SEQ ID NO:3, and amino acids 2-50 of SEQ ID NO:2 and (b) a conjugate comprising an antibody attached to a signal-generating compound capable of generating a detectable signal.

In a seventeenth aspect, the invention is directed to kits for determining the presence of antibody to *P. malariae, P. ovale, P. vivax* and *P. falciparum* in a test sample comprising: (a) an antigen comprising an amino acid sequence selected from the group consisting of SEQ ID NO:2, SEQ ID NO:3, and amino acids 2-50 of SEQ ID NO:2, a *P. ovale* antigen, a *P. malariae* antigen and a *P. falciparum* antigen and (b) a conjugate comprising an antibody attached to a signal generating compound capable of generating a detectable signal.

In an eighteenth aspect, the invention is directed to kits for detecting antibodies to *P. malariae, P. ovale, P. vivax* and *P. falciparum* in a test sample comprising: a) an anti-antibody and b) an antigen comprising an amino acid sequence selected from the group consisting of SEQ ID NO:2, SEQ ID NO:3, and amino acids 2-50 of SEQ ID NO:2, a *P. ovale* antigen, a *P. malariae* antigen and a *P. falciparum* antigen and b) a conjugate comprising an antibody attached to a signal generating compound capable of generating a detectable signal.

In an nineteenth aspect, the invention is further directed to kits for detecting antibodies to *P. malariae, P. ovale, P. vivax* and *P. falciparum* in a test sample comprising: (a) an anti-antibody and (b) a first conjugate comprising an antigen comprising an amino acid sequence selected from the group consisting of SEQ ID NO:2, SEQ ID NO:3, and amino acids 2-50 of SEQ ID NO:2, attached to a signal generating compound capable of generating a detectable signal, a second conjugate comprising a *P. ovale* antigen attached to a signal generating compound capable of generating a detectable signal; a third conjugate comprising a *P. malariae* antigen attached to a signal generating compound capable of generating a detectable signal and a fourth conjugate comprising a *P. falciparum* antigen attached to a signal generating compound capable of generating a detectable signal.

In a twentieth aspect, the invention is directed to methods of detecting the presence of *P. vivax* antibodies in a test sample suspected of containing the antibodies comprising the steps of:

(a) contacting the test sample with anti-antibody for a time and under conditions sufficient to allow for formation of anti-antibody/*P. vivax* antibody complexes;

(b) adding antigen to the resulting anti-antibody/*P. vivax* antibody complexes for a time and under conditions sufficient to allow the antigen to bind to bound antibody, wherein the antigen comprises an amino acid sequence selected from the group consisting of SEQ ID NO:2, SEQ ID NO:3, and amino acids 2-50 of SEQ ID NO:2, wherein the antigen is conjugated to a signal generating compound capable of generating a detectable signal; and (c) detecting presence of antibodies which can be present in the test sample by detecting presence of the signal generated by the signal generating compound.

BRIEF DESCRIPTION OF THE FIGURES

FIG. 1A shows the polynucleotide sequence of the optimized *Plasmodium vivax* "Exported Protein 1" (EXP1) gene (SEQ ID NO:1). FIG. 1B shows the amino acid sequence (SEQ ID NO:2) of the EXP1 protein encoded by the EXP1 gene shown in FIG. 1A (SEQ ID NO:1). FIG. 1C shows a synthetic fragment (SEQ ID NO:3) constituting the C-terminal portion of the EXP1 protein shown in FIG. 1B (SEQ ID NO:2).

DETAILED DESCRIPTION

Figure 2:
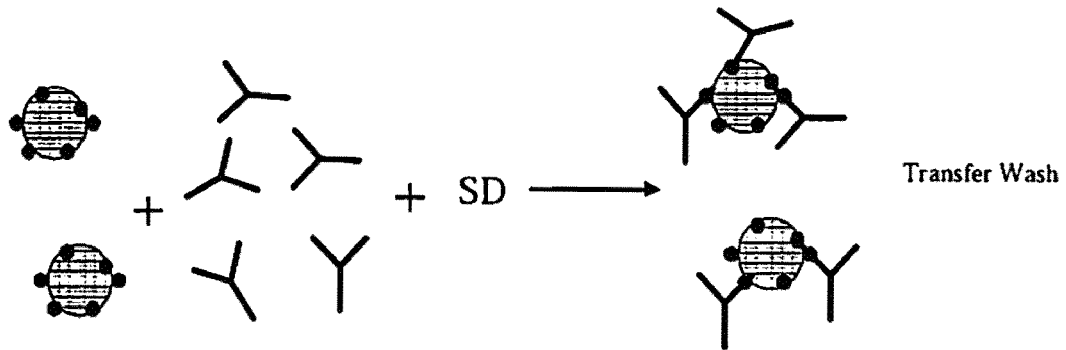
FIG. 2 shows the assay format described in Example 9.
Figure 2:
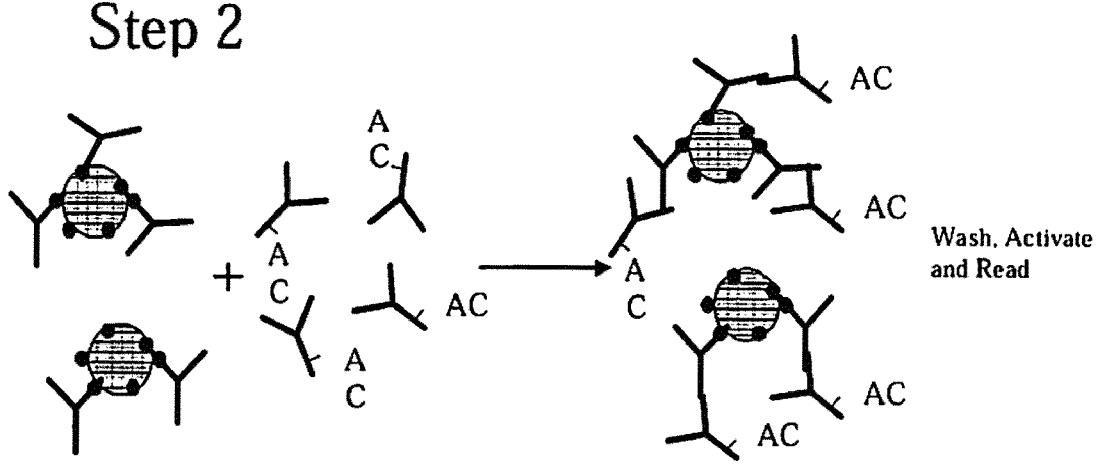
Figure 2:
Figure 2:
Figure 2:

The subject invention relates to novel nucleic acid and polypeptide sequences designed from *P. vivax*. Such nucleic acid sequences and polypeptides can be used for diagnostic as well as therapeutic purposes.

Polynucleotide Sequence and Encoded Polypeptides

The inventors found that anti-EXP1 antibodies are present within days or weeks of *P. vivax* infection. These antibodies do not appear to persist since they are difficult to detect in serum samples taken from individuals who recovered from malaria years earlier. Thus, anti-EXP1 IgG is a marker of recent infection, which can be critical to identification of antibodies among blood donors who recently traveled to malaria endemic area(s).

The invention is directed in part to novel polynucleotides and polypeptides that are useful, for example, for detecting *P. vivax* infection of a subject. The polynucleotides and polypeptides of the invention are particularly useful for identifying those subjects that have been recently infected with *P. vivax*. Thus the invention provides diagnostic tools, as well as tools to screen samples from subjects, such as tissues, including, for example, blood. Detecting recent *P. vivax* infection allows for removing unfit harvested blood from the blood supply, thus protecting recipient subjects.

The current invention has the advantage that EXP1 recombinant polypeptides can be used for specific detection of antibodies in serum or plasma of individuals infected with *P. vivax* within days or weeks of infection. Thus, as a marker of early (acute) phase infection, the EXP1 polypeptides have the ability to identify individuals recently exposed to *P. vivax*. Since these individuals may be blood donors, detection of antibodies soon after seroconversion reduces the risk of transfusion-transmitted malaria.

The inventors accomplished the invention by accurately predicting the polynucleotide sequence that encodes the C-terminal portion of the *P. vivax* EXP1 polypeptide, and then testing the abilities of the encoded polypeptides to bind anti-EXP1 antibodies, including those antibodies from samples harvested from subjects.

In one embodiment, a recombinant EXP1 polypeptide fused with an amino terminal CKS sequence and used in an indirect ELISA detects anti-EXP1 IgG and IgM antibodies in individuals infected with *P. vivax*.

In one embodiment, a recombinant EXP1 polypeptide of the invention is coated onto a solid phase support and used to capture antibodies present in serum or plasma. Anti-immunoglobulin conjugate is used to detect bound immunoglobulin.

The sequence of the encoded EXP1 protein for *P. vivax* was predicted by sequence homology with the *P. falciparum* and *P. yoelii* proteins, and by identifying potential splice sites from the *P. vivax* genomic sequence. The polynucleotide sequence of the invention for *P. vivax* EXP1 synthetic gene is shown in FIG. 1A (SEQ ID NO:1), and the encoded amino acid sequence is shown in FIG. 1B (SEQ ID NO:2); these sequences are also shown in Table A which also indicates specific features. The gene contains a 5'-EcoRI site followed by a start codon (underlined), the body of the gene encoding the predicted C-terminal amino acid sequence of *P. vivax* EXP1, a sequence encoding a histidine tag (italicized), a stop codon (boldface) and a BamHI site. The restriction enzyme sites were used for cloning into expression vectors, and the histidine tag was included to facilitate subsequent purification of the expressed protein. The compositions and methods of the invention comprise the unmodified polynucleotide and polypeptide sequences, wherein the histidine tag is removed as well as those polypeptides lacking the initial methionine and His tag, such as that of SEQ ID NO:3.

TABLE A

EXP1 polynucleotide (SEQ ID NO: 1) and encoded polypeptide (SEQ ID NO: 2)

```
gaattcc atg aac gcc ggt aac ggt cgt cat cca ttt tct ctg ggt ggt ggt aaa ggt ggc      61
        Met Asn Ala Gly Asn Gly Arg His Pro Phe Ser Leu Gly Gly Gly Lys Gly Gly       18 gac gcg gcg cct acg gag ccg acg ccg gca ccg acc gcg ccg agc gca act ggt ctg aac     121
Asp Ala Ala Pro Thr Glu Pro Thr Pro Ala Pro Thr Ala Pro Ser Ala Thr Gly Leu Asn      38 gat gac ggt tct tct tct ggc act gaa tct act tct cat cat cac cat cac cat tga gga    181
Asp Asp Gly Ser Ser Ser Gly Thr Glu Ser Thr Ser His His His His His His             56 tcc                                                                                  184
```

The invention also relates to polypeptides comprising amino acid sequences that are at least about 70% identical to, preferably at least about 80% identical to, and more preferably at least about 90% identical to the amino acid sequence of SEQ ID NO: 2 or 3 or to residues 2-50 of SEQ ID NO: 2.

The invention encompasses "fragments" and "peptides" of the full-length polypeptides described herein. Such peptides represent portions of the polypeptide that have, for example, specific immunogenic or binding properties. A fragment can be between 3-10 amino acids, 10-20 amino acids, 20-40 amino acids, 40-56 amino acids in length or even longer. Amino acid sequences having at least 70% amino acid identity, preferably at least 80% amino acid identity, and more preferably at least 90% identity to the fragments described herein are also included within the scope of the present invention.

An "epitope" is an antigenic determinant of a polypeptide. An epitope may comprise at least three amino acids in a spatial conformation that is unique to the epitope. Generally, an epitope consists of at least five such amino acids, and more usually, consists of at least eight to ten amino acids.

Furthermore, the present invention encompasses fragments and derivatives of the nucleic acid sequences of the present invention, as well as fragments and portions of the amino acid sequences of the present invention. The invention also encompasses functional equivalents of the sequences of the invention (i.e., polynucleotide sequences encoding proteins having, for example, the same binding affinities, epitopes, etc. of the encoded proteins).

The invention is also directed to methods of detecting recent *P. vivax* infections, wherein a test sample from a subject is analyzed for the presence of anti-*P. vivax* EXP1 antibodies. Using anti-EXP1 antibodies to detect recent *P. vivax* infections is effective because anti-EXP1 polypeptide antibodies are at their highest titers and most easily detectable in subjects who have been recently infected, but the titer decreases over time to mostly undetectable levels. The test sample is contacted with an EXP1 polypeptide, and then binding of the EXP1 polypeptide by antibodies present in the test sample is detected. In one embodiment, the EXP1 polypeptides are linked to a substrate.

Definitions

"Specifically hybridize" refers to the ability of a nucleic acid to bind detectably and specifically to a second nucleic acid. Polynucleotides specifically hybridize with target nucleic acid strands under hybridization and wash conditions that minimize appreciable amounts of detectable binding by non-specific nucleic acids.

"Target sequence" or "target nucleic acid sequence" means a nucleic acid sequence encoding a P. vivax EXP1 polypeptide, or complements thereof, that is amplified, detected, or both using, for example, complementary polynucleotides. Additionally, while the term target sequence sometimes refers to a double stranded nucleic acid sequence, a target sequence can also be single-stranded. In cases where the target is double-stranded, polynucleotide primer sequences of the present invention preferably amplify both strands of the target sequence.

"Test sample" means a sample taken from a subject, or a biological fluid, wherein the sample may contain P. vivax polypeptide or anti P. vivax polypeptide antibody. A test sample can be taken from any source, for example, tissue, blood, saliva, sputa, mucus, sweat, urine, urethral swabs, cervical swabs, urogenital or anal swabs, conjunctival swabs, ocular lens fluid, cerebral spinal fluid, etc. A test sample can be used (i) directly as obtained from the source; or (ii) following a pre-treatment to modify the character of the sample. Thus, a test sample can be pre-treated prior to use by, for example, preparing plasma or serum from blood, disrupting cells or viral particles, preparing liquids from solid materials, diluting viscous fluids, filtering liquids, adding reagents, purifying nucleic acids, etc.

"Subjects" include a mammal, a bird, or a reptile. The subject can be a cow, horse, dog, cat, or a primate. Subject can also be a human. Subjects can be alive or dead.

A "polynucleotide" is a nucleic acid polymer of ribonucleic acid (RNA), deoxyribonucleic acid (DNA), modified RNA or DNA, or RNA or DNA mimetics (such as PNAs), and derivatives thereof, and homologues thereof. Thus, polynucleotides include polymers composed of naturally occurring nucleobases, sugars and covalent inter-nucleoside (backbone) linkages as well as polymers having non-naturally-occurring portions that function similarly. Such modified or substituted nucleic acid polymers are well known in the art and for the purposes of the present invention, are referred to as "analogues." Oligonucleotides are generally short polynucleotides from about 10 to up to about 160 or 200 nucleotides.

A "variant polynucleotide" or a "variant nucleic acid sequence" means a polynucleotide having at least about 60% nucleic acid sequence identity, more preferably at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% nucleic acid sequence identity and yet more preferably at least about 99% nucleic acid sequence identity with the nucleic acid sequence of SEQ ID NO:1. Variants do not encompass the native nucleotide sequence. Other variant polynucleotides include those that differ from SEQ ID NO: 1, but because of the redundancy of the genetic code, encode a polypeptide of SEQ ID No: 2 or 3, or amino acids 2-50 of SEQ ID No: 2, fragments of variants thereof.

Ordinarily, variant polynucleotides are at least about 8 nucleotides in length, often at least about 9, 10, 11, 12, 13, 14, 15, 16, 17, 18, 19, 20, 21, 22, 23, 24, 25, 26, 27, 28, 29 30, 35, 40, 45, 50, 55, 60 nucleotides in length, or even about 75-200 nucleotides in length, or more.

"Percent (%) nucleic acid sequence identity" with respect to nucleic acid sequences is defined as the percentage of nucleotides in a candidate sequence that are identical with the nucleotides in the sequence of interest, after aligning the sequences and introducing gaps, if necessary, to achieve the maximum percent sequence identity. Alignment for purposes of determining % nucleic acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

When nucleotide sequences are aligned, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) can be calculated as follows:

$$\% \text{ nucleic acid sequence identity} = W/Z \cdot 100$$

where

W is the number of nucleotides cored as identical matches by the sequence alignment program's or algorithm's alignment of C and D and Z is the total number of nucleotides in D.

When the length of nucleic acid sequence C is not equal to the length of nucleic acid sequence D, the % nucleic acid sequence identity of C to D will not equal the % nucleic acid sequence identity of D to C.

"Consisting essentially of a polynucleotide having a % sequence identity" means that the polynucleotide does not substantially differ in length, but may differ substantially in sequence. Thus, a polynucleotide "A" consisting essentially of a polynucleotide having at least 80% sequence identity to a known sequence "B" of 100 nucleotides means that polynucleotide "A" is about 100 nts long, but up to 20 nts can vary from the "B" sequence. The polynucleotide sequence in question can be longer or shorter due to modification of the termini, such as, for example, the addition of 1-15 nucleotides to produce specific types of probes, primers and other molecular tools, etc., such as the case of when substantially non-identical sequences are added to create intended secondary structures. Such non-identical nucleotides are not considered in the calculation of sequence identity when the sequence is modified by "consisting essentially of"

The specificity of single stranded DNA to hybridize complementary fragments is determined by the stringency of the reaction conditions. Hybridization stringency increases as the propensity to form DNA duplexes decreases. In nucleic acid hybridization reactions, the stringency can be chosen to favor specific hybridizations (high stringency). Less-specific hybridizations (low stringency) can be used to identify related, but not exact, DNA molecules (homologous, but not identical) or segments.

DNA duplexes are stabilized by: (1) the number of complementary base pairs, (2) the type of base pairs, (3) salt concentration (ionic strength) of the reaction mixture, (4) the temperature of the reaction, and (5) the presence of certain organic solvents, such as formamide, which decrease DNA duplex stability. A common approach is to vary the temperature: higher relative temperatures result in more stringent reaction conditions.(Ausubel et al., 1987) provide an excellent explanation of stringency of hybridization reactions.

Hybridization under "stringent conditions" means hybridization protocols in which nucleotide sequences at least 60% homologous to each other remain hybridized.

Polynucleotides can include other appended groups such as peptides (e.g., for targeting host cell receptors in vivo), or agents facilitating transport across the cell membrane. In addition, oligonucleotides can be modified with hybridization-triggered cleavage agents (van der Krol et al., 1988) or intercalating agents (Zon, 1988). The oligonucleotide can be conjugated to another molecule, e.g., a peptide, a hybridization triggered cross-linking agent, a transport agent, a hybridization-triggered cleavage agent, and the like.

Useful polynucleotide analogues include polymers having modified backbones or non-natural inter-nucleoside linkages. Modified backbones include those retaining a phosphorus atom in the backbone, such as phosphorothioates, chiral phosphorothioates, phosphorodithioates, phosphotriesters, aminoalkylphosphotriesters, methyl and other alkyl phosphonates, as well as those no longer having a phosphorus atom, such as backbones formed by short chain alkyl or cycloalkyl inter-nucleoside linkages, mixed heteroatom and alkyl or cycloalkyl inter-nucleoside linkages, or one or more short chain heteroatomic or heterocyclic inter-nucleoside linkages. Modified nucleic acid polymers (analogues) can contain one or more modified sugar moieties.

Analogs that are RNA or DNA mimetics, in which both the sugar and the inter-nucleoside linkage of the nucleotide units are replaced with novel groups, are also useful. In these mimetics, the base units are maintained for hybridization with the target sequence. An example of such a mimetic, which has been shown to have excellent hybridization properties, is a peptide nucleic acid (PNA) (Buchardt et al., 1992; Nielsen et al., 1991).

The realm of nucleotides includes derivatives wherein the nucleic acid molecule has been covalently modified by substitution, chemical, enzymatic, or other appropriate means with a moiety other than a naturally occurring nucleotide.

The polynucleotide of SEQ ID NO:1 can be prepared by conventional techniques, such as solid-phase synthesis using commercially available equipment, such as that available from Applied Biosystems USA Inc. (Foster City, Calif.; USA), DuPont, (Wilmington, Del.; USA), or Milligen (Bedford, Mass.; USA). Modified polynucleotides, such as phosphorothioates and alkylated derivatives, can also be readily prepared by similar methods known in the art (Fino, 1995; Mattingly, 1995; Ruth, 1990).

"Identity between two amino acid sequences" is defined as the presence of a series of exactly alike or invariant amino acid residues in both sequences (see above definition for identity between nucleic acid sequences). The definitions of "complementarity" and "identity" are well known to those of ordinary skill in the art.

"Encoded by" refers to a nucleic acid sequence which codes for a polypeptide sequence, wherein the polypeptide sequence or a portion thereof contains an amino acid sequence of at least 3 amino acids, more preferably at least 8 amino acids, and even more preferably at least 15 amino acids from a polypeptide encoded by the nucleic acid sequence.

The present invention also encompasses isolated polynucleotide sequences that encode a polypeptide having functional activity similar to that of SEQ ID NOs:2 and 3, and that are hybridizable, under moderately stringent conditions, to a polynucleotide having a nucleic sequence comprising, or complementary to, the nucleotide sequences described above.

The terms "fragment or subfragment that is functionally equivalent" and "functionally equivalent fragment or subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric constructs to produce the desired phenotype in a transformed plant. Chimeric constructs can be designed for use in co-suppression or antisense by linking a nucleic acid fragment or subfragment thereof, whether or not it encodes an active protein, in the appropriate orientation relative to a promoter sequence.

The terms "homology", "homologous", "substantially similar" and "corresponding substantially" are used interchangeably herein. They refer to nucleic acid fragments wherein changes in one or more nucleotide bases does not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences described herein.

"Gene" refers to a nucleic acid fragment that expresses a specific protein, including regulatory sequences preceding (5' non-coding sequences) and following (3' non-coding sequences) the coding sequence.

"Native gene" refers to a gene as found in nature with its own regulatory sequences. In contrast, "chimeric construct" refers to a combination of nucleic acid fragments that are not normally found together in nature. Accordingly, a chimeric construct may comprise regulatory sequences and coding sequences that are derived from different sources, or regulatory sequences and coding sequences derived from the same source, but arranged in a manner different than that normally found in nature. (The term "isolated" means that the sequence is removed from its natural environment.)

A "foreign" gene refers to a gene not normally found in the host organism, but that is introduced into the host organism by gene transfer. Foreign genes can comprise native genes inserted into a non-native organism, or chimeric constructs. A "transgene" is a gene that has been introduced into the genome by a transformation procedure.

A "probe" or "primer" as used herein is a polynucleotide that is at least 8 nucleotides in length and forms a hybrid structure with a target sequence, due to complementarity of at least one sequence in the probe or primer with a sequence in the target region. The polynucleotide regions of the probe can be composed of DNA and/or RNA and/or synthetic nucleotide analogs. Preferably, the probe does not contain a sequence that is complementary to the sequence or sequences used to prime for a target sequence during the polymerase chain reaction.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" (or "regulatory sequence") refers to a DNA sequence capable of controlling the expression of a coding sequence or functional RNA. The promoter sequence, for example, consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue-specificity of a promoter. Regulatory sequences (e.g., a promoter) can also be located within the transcribed portions of genes, and/or downstream of the transcribed sequences. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types, at most times, are commonly referred to as "constitutive promoters". New promoters of various types useful in plant cells are constantly being discovered; numerous examples may be found in the compilation in Okamura et al. (1989) (Okamura and Goldberg, 1989). It is further recognized that since, in most cases, the exact boundaries of regulatory sequences have not been completely defined, DNA fragments of some variation may have identical promoter activity.

"Intron" is an intervening sequence in a gene that does not encode a portion of the protein sequence. Thus, such sequences are transcribed into RNA but are then excised and are not translated. The term is also used for the excised RNA sequences. An "exon" is a portion of the gene sequence that is transcribed and is found in the mature messenger RNA derived from the gene, but is not necessarily a part of the sequence that encodes the final gene product.

"Translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster, 1995).

"3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a DNA that is complementary to and synthesized from a mRNA template using the enzyme reverse transcriptase. The cDNA can be single-stranded or converted into the double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

"Endogenous RNA" refers to any RNA which is encoded by any nucleic acid sequence present in the genome of the host prior to transformation with the recombinant construct of the present invention, whether naturally-occurring or non-naturally occurring, i.e., introduced by recombinant means, mutagenesis, etc.

"Non-naturally occurring" means artificial, not consistent with what is normally found in nature.

"Operably-linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

"Expression," as used herein, refers to the production of a functional end-product. Expression of a gene involves transcription of the gene and translation of the mRNA into a precursor or mature protein. "Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020).

"Mature" protein refers to a post-translationally processed polypeptide; i.e., one from which any pre- or pro-peptides present in the primary translation product have been removed. "Precursor" protein refers to the primary product of translation of mRNA; i.e., with pre- and pro-peptides still present. Pre- and pro-peptides may be but are not limited to intracellular localization signals.

"Stable transformation" refers to the transfer of a nucleic acid fragment into a genome of a host organism, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms. The term "transformation" as used herein refers to both stable transformation and transient transformation.

Standard recombinant DNA and molecular cloning techniques used herein are well known in the art and are described more fully in Sambrook et al. (1989) (Sambrook, 1989) (hereinafter "Sambrook").

"Recombinant" refers to an artificial combination of two otherwise separated segments of sequence, e.g., by chemical synthesis or by the manipulation of isolated segments of nucleic acids by genetic engineering techniques.

"PCR" or "Polymerase Chain Reaction" is a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps is referred to as a cycle.

PCR is a powerful technique used to amplify DNA millions of fold, by repeated replication of a template, in a short period of time. ((Mullis et al., 1986); Erlich et al., European Patent Application No. 50,424; European Patent Application No. 84,796; European Patent Application No. 258,017, European Patent Application No. 237,362; European Patent Application No. 201,184, U.S. Pat. No. 4,683,202; U.S. Pat. No. 4,582,788; and U.S. Pat. No. 4,683,194). The process utilizes sets of specific in vitro synthesized oligonucleotides to prime DNA synthesis. The design of the primers is dependent upon the sequences of DNA that are to be analyzed. The technique is carried out through many cycles (usually 20-50) of melting the template at high temperature, allowing the primers to anneal to complementary sequences within the template and then replicating the template with DNA polymerase.

The products of PCR reactions are analyzed by separation in agarose gels followed by ethidium bromide staining and visualization with UV transillumination. Alternatively, radioactive dNTPs can be added to the PCR in order to incorporate label into the products. In this case the products of PCR are visualized by exposure of the gel to x-ray film. The added advantage of radiolabeling PCR products is that the levels of individual amplification products can be quantitated.

"Recombinant construct", "expression construct" and "recombinant expression construct" are used interchangeably herein. These terms refer to a functional unit of genetic material that can be inserted into the genome of a cell using standard methodology well known to one skilled in the art. Such a construct may be itself or may be used in conjunction with a vector. If a vector is used, then the choice of vector is dependent upon the method that will be used to transform host plants, as is well known to those skilled in the art. For example, a plasmid can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., 1985); De Almeida, 1989 #475}), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

Polypeptide Variants

In general, a polypeptide variant preserves antigenic function and includes any variant in which residues at a particular position in the sequence have been substituted by other amino acids, and further includes the possibility of inserting an additional residue or residues between two residues of the parent polypeptide as well as the possibility of deleting one or more residues from the parent sequence.

"A polypeptide variant" means a polypeptide comprising an amino acid sequence of SEQ ID NO:2, SEQ ID NO:3, or residues 2-50 of SEQ ID NO:2 having at least about 70% amino acid sequence identity with a full-length native sequence or a fragment of a full-length polypeptide sequence. For example, polypeptide variants include those wherein one or more amino acid residues are added or deleted at the N- or C-terminus of the full-length native amino acid sequence. A polypeptide variant will have at least about 71%-75% amino acid sequence identity; at least about 76%-79% amino acid sequence identity; at least about 80% amino acid sequence identity, at least about 81% amino acid sequence identity, at least about 82%, 83%, 84%, 85%, 86%, 87%, 88%, 89%, 90%, 91%, 92%, 93%, 94%, 95%, 96%, 97%, 98% amino acid sequence identity and at least about 99% amino acid sequence identity with a full-length sequence. Ordinarily, variant polypeptides are at least about 10 amino acids in length, often at least about 20 amino acids in length, more often at least about 30, 40, 50, 60, 70, 80, 90, 100, 150, 200, or 300 amino acids in length, or more.

"Percent (%) amino acid sequence identity" is defined as the percentage of amino acid residues that are identical with amino acid residues in a target sequence in a candidate sequence when the two sequences are aligned. To determine % amino acid identity, sequences are aligned and if necessary, gaps are introduced to achieve the maximum % sequence identity; conservative substitutions are not considered as part of the sequence identity. Amino acid sequence alignment procedures to determine percent identity are well known to those of skill in the art. Publicly available computer software such as BLAST, BLAST2, ALIGN2 or Megalign (DNASTAR) can be used to align polypeptide sequences. Those skilled in the art can determine appropriate parameters for measuring alignment, including any algorithms needed to achieve maximal alignment over the full length of the sequences being compared.

When amino acid sequences are aligned, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) can be calculated as: % amino acid sequence identity=X/Y100 where

X is the number of amino acid residues scored as identical matches by the sequence alignment program's or algorithm's alignment of A and B and Y is the total number of amino acid residues in B.

If the length of amino acid sequence A is not equal to the length of amino acid sequence B, the % amino acid sequence identity of A to B will not equal the % amino acid sequence identity of B to A.

Useful conservative substitutions are shown in Table B, "Exemplary substitutions." Conservative substitutions whereby an amino acid of one class is replaced with another amino acid of the same type fall within the scope of the subject invention so long as the substitution does not materially alter the biological activity of the compound. If such substitutions result in a change in biological activity, then more substantial changes, indicated in Table C as exemplary are introduced and the products screened for target sequence biological activity.

TABLE B

Exemplary substitutions

| Original residue | Exemplary substitutions | Preferred substitutions |
| --- | --- | --- |
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala, Tyr | Leu |
| Pro (P) | Ala | Ala |
| Ser (S) | Thr | Thr |
| Thr (T) | Ser | Ser |
| Trp (W) | Tyr, Phe | Tyr |
| Tyr (Y) | Trp, Phe, Thr, Ser | Phe |
| Val (V) | Ile, Leu, Met, Phe, Ala, Norleucine | Leu |

Non-conservative substitutions that affect (1) the structure of the polypeptide backbone, such as a beta-sheet or alpha-helical conformation, (2) the charge or (3) hydrophobicity, or (4) the bulk of the side chain of the target site can modify polypeptide function. Residues are divided into groups based on common side-chain properties as denoted in Table B. Non-conservative substitutions entail exchanging a member of one of these classes for another class. Substitutions can be introduced into conservative substitution sites or more usually into non-conserved sites.

TABLE C

Amino acid classes

| Class | Amino acids |
| --- | --- |
| hydrophobic | Norleucine, Met, Ala, Val, Leu, Ile |
| neutral hydrophilic | Cys, Ser, Thr |
| acidic | Asp, Glu |
| basic | Asn, Gln, His, Lys, Arg |
| disrupt chain formation | Gly, Pro |
| aromatic | Trp, Tyr, Phe |

The variant polypeptides can be made using, for example, oligonucleotide-mediated (site-directed) mutagenesis, alanine scanning, and PCR mutagenesis. Site-directed mutagenesis (Carter, 1986; Zoller and Smith, 1987), cassette mutagenesis, restriction selection mutagenesis (Wells et al., 1985) or other known techniques can be performed on the cloned DNA to produce target sequence variants (Ausubel et al., 1987; Sambrook, 1989).

Isolated/Purified Polypeptides

An "isolated" or "purified" polypeptide or biologically active fragment (such as an Fab fragment) is separated and/or recovered from a component of its environment. Contaminant components include materials that would typically interfere with diagnostic uses for the polypeptide, and can include enzymes, hormones, and other polypeptideaceous or non-polypeptideaceous materials. To be substantially isolated, preparations having less than 30% by dry weight of contaminants, usually less than 20%, 10% and more often, less than 5% contaminants. An isolated, recombinantly-produced target sequence or biologically active portion is desirably substantially free of culture medium, i.e., culture medium represents less than 20%, 10% or 5% of the volume of the target sequence preparation.

The polypeptides of the invention can be either synthesized in vitro or expressed recombinantly from the polynucleotide sequences. Because of redundancy in the genetic code, the sequences need not be identical to practice the invention. Polynucleotide and polypeptide sequence identities can be from 70%-100%, such as 70%, 75%, 80%, 81%, 82%, 83%, 84%, 85%, 86%, 87%, 88%, 89%, 90%, 91%, 92%, 93%, 94%, 95%, 96%, 97%, 98%, 99% and of course, 100%.

The polypeptides of the invention can be readily synthesized in vitro using polypeptide chemistry. For example, polypeptide synthesis can be carried out in a stepwise manner on a solid phase support using an automated polypeptide synthesizer, such as a Rainin Symphony Peptide Synthesizer, Advanced Chemtech Peptide Synthesizer, Argonaut Parallel Synthesis System, or an Applied Biosystems Peptide Synthesizer. The peptide synthesizer instrument combines the Fmoc chemistry with HOBt/HBTU/DIEA activation to perform solid-phase peptide synthesis.

The side chains of many amino acids contain chemically reactive groups, such as amines, alcohols, or thiols. These side chains must be additionally protected to prevent undesired side-reactions during the coupling step. Side chain protecting groups that are base-stable, more preferably, both base-stabile and acid-labile are most useful.

Alternatively, a polypeptide of interest can be introduced into either a prokaryotic or eukaryotic host cell, through the use of a vector or construct, in order for the host cell to express the protein of interest. The vector, for example, a bacteriophage, cosmid or plasmid, may comprise the nucleic acid sequence encoding the enzyme, as well as any regulatory sequence (e.g., promoter) that is functional in the host cell and is able to elicit expression of the protein encoded by the nucleic acid sequence. The regulatory sequence (e.g., promoter) is in operable association with, or operably linked to, the nucleotide sequence. (A regulatory sequence (e.g., promoter) is said to be "operably linked" with a coding sequence if the regulatory sequence affects transcription or expression of the coding sequence.) Suitable promoters include, for example, those from genes encoding alcohol dehydrogenase, glyceraldehyde-3-phosphate dehydrogenase, phosphoglucoisomerase, phosphoglycerate kinase, acid phosphatase, T7, TPI, lactase, metallothionein, cytomegalovirus immediate early, whey acidic protein, glucoamylase, promoters activated in the presence of galactose, for example, GAL1 and GAL10, as well as any other promoters involved in prokaryotic and eukaryotic expression systems. Additionally, nucleic acid sequences that encode other proteins may also be included within the vector as well as other non-promoter regulatory sequences such as, for example, a polyadenylation signal (e.g., the poly-A signal of SV-40T-antigen, ovalalbumin or bovine growth hormone). The choice of sequences present in the construct is dependent upon the desired expression products as well as the nature of the host cell.

As noted above, once the vector has been constructed, it may then be introduced into the host cell of choice by methods known to those of ordinary skill in the art including, for example, transfection, transformation and electroporation (Sambrook, 1989). The host cell is then cultured under suitable conditions permitting expression of the desired protein that is then recovered and purified.

Examples of suitable prokaryotic host cells include, for example, bacteria such as *Escherichia coli*, *Bacillus subtilis*, Actinomycetes such as *Streptomyces coelicolor*, *Streptomyces lividans*, as well as cyanobacteria such as *Spirulina* spp.

(i.e., blue-green algae). Examples of suitable eukaryotic host cells include, for example, mammalian cells, plant cells, yeast cells such as *Saccharomyces* spp., *Lipomyces* spp., *Candida* spp., such as *Yarrowia* (*Candida*) spp., *Kluyveromyces* spp., *Pichia* spp., *Trichoderma* spp. or *Hansenula* spp., or fungal cells such as filamentous fungal cells, for example, *Aspergillus, Neurospora* and *Penicillium*. Insect cells, such as those used in Baculovirus systems (Luckow, 1991), are also useful for in vitro production of polypeptides with eukaryotic modifications.

Expression in a host cell can be accomplished in a transient or stable fashion. Transient expression can occur from introduced constructs which contain expression signals functional in the host cell, but which constructs do not replicate and rarely integrate in the host cell, or where the host cell is not proliferating. Transient expression also can be accomplished by inducing the activity of a regulatable promoter operably linked to the gene of interest, although such inducible systems frequently exhibit a low basal level of expression. Stable expression can be achieved by introduction of a construct that can integrate into the host genome or that autonomously replicates in the host cell. Stable expression of the gene of interest can be selected for through the use of a selectable marker located on or transfected with the expression construct, followed by selection for cells expressing the marker. When stable expression results from integration, the site of the construct's integration can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

A transgenic mammal can also be used in order to express the protein of interest encoded by one or both of the above-described nucleic acid sequences. More specifically, once the above-described construct is created, it can be inserted into the pronucleus of an embryo. The embryo can then be implanted into a recipient female. Alternatively, a nuclear transfer method could also be utilized (Schnieke et al., 1997). Gestation and birth are then permitted to occur (see, e.g., U.S. Pat. No. 5,750,176 and U.S. Pat. No. 5,700,671), and milk, tissue or other fluid samples from the offspring should then contain the protein of interest. The mammal utilized as the host can be selected from the group consisting of, for example, a mouse, a rat, a rabbit, a pig, a goat, a sheep, a horse and a cow. However, any mammal can be used provided it has the ability to incorporate DNA encoding the protein of interest into its genome.

Use of the Polynucleotides and Polypeptides of the Invention

The isolated nucleic acid sequences and the corresponding proteins encoded thereby have many beneficial uses. The present invention provides immunoassays and, in particular, antigens that accurately detect the presence of antibodies to *P. vivax* in human sera.

Furthermore, the present invention also includes polyclonal and monoclonal antibodies raised against the above-described proteins. Such an antibody can be used, for example, in an immunoassay, a vaccine (for passive immunization), a kit, or for research purposes.

Immunoassays

There are two basic types of assays, competitive and non-competitive (e.g., immunometric and sandwich, respectively). In both assays, antibody or antigen reagents are covalently or non-covalently attached to the solid phase (Wild, 2001) Linking agents for covalent attachment are known and can be part of the solid phase or derivatized to it prior to coating. Examples of solid phases used in immunoassays are porous and non-porous materials, latex particles, magnetic particles, microparticles, strips, beads, membranes, microtiter wells and plastic tubes. The choice of solid phase material and method of labeling the antigen or antibody reagent are determined based upon desired assay format performance characteristics. For some immunoassays, no label is required. For example, if the antigen is on a detectable particle such as a red blood cell, reactivity can be established based upon agglutination. Alternatively, an antigen-antibody reaction can result in a visible change (e.g., radial immunodiffusion). In most cases, one of the antibody or antigen reagents used in an immunoassay is attached to a signal generating compound or "label". This signal generating compound or label is in itself detectable or can be reacted with one or more additional compounds to generate a detectable product (see also U.S. Pat. No. 6,395,472 B1). Examples of such signal generating compounds include chromogens, radioisotopes (e.g., $^{125}$I, $^{131}$I, $^{32}$P, $^{3}$H, $^{35}$S, and $^{14}$C), fluorescent compounds (e.g., chromogens, radioisotopes (e.g., and C), fluorescent compounds (e.g., fluorescein, rhodamine), chemiluminescent compounds, particles (visible or fluorescent), nucleic acids, complexing agents, or catalysts such as enzymes (e.g., alkaline phosphatase, acid phosphatase, horseradish peroxidase, beta-galactosidase, and ribonuclease). In the case of enzyme use, addition of chromo-, fluoro-, or lumo-genic substrate results in generation of a detectable signal. Other detection systems such as time-resolved fluorescence, internal-reflection fluorescence, amplification (e.g., polymerase chain reaction) and Raman spectroscopy are also useful.

There are two general formats commonly used to monitor specific antibody titer and type in humans: (1) antigen is presented on a solid phase, as described above, the human biological fluid containing the specific antibodies is allowed to react with the antigen, and then antibody bound to antigen is detected with an anti-human antibody coupled to a signal generating compound, and (2) an anti-human antibody is bound to the solid phase, the human biological fluid containing specific antibodies is allowed to react with the bound antibody, and then antigen attached to a signal generating compound is added to detect specific antibody present in the fluid sample. In both formats, the anti-human antibody reagent can recognize all antibody classes, or alternatively, be specific for a particular class or subclass of antibody, depending upon the intended purpose of the assay. These assays formats as well as other known formats are intended to be within the scope of the present invention and are well known to those of ordinary skill in the art.

Any of the exemplary formats herein and any assay or kit according to the invention can be adapted or optimized for use in automated and semi-automated systems (including those in which there is a solid phase comprising a microparticle), as described, e.g., in U.S. Pat. Nos. 5,089,424 and 5,006,309, and as, e.g., commercially marketed by Abbott Laboratories (Abbott Park, Ill.) including but not limited to Abbott's ARCHITECT®, AxSYM, IMX, PRISM, and Quantum II platforms, as well as other platforms.

The assays and kits of the present invention can be adapted or optimized for point of care assay systems, including Abbott's Point of Care (i-STAT™) electrochemical immunoassay system. Immunosensors and methods of manufacturing and operating them in single-use test devices are described, for example in U.S. Pat. No. 5,063,081 and published U.S. Patent Application Nos. 20030170881, 20040018577, 20050054078, and 20060160164 (incorporated by reference herein for their teachings regarding same).

The present invention includes a method of detecting antibodies to *P. vivax* in a test sample comprising the steps of: (a) contacting the test sample suspected of containing the antibodies with a *P. vivax* protein or antigen comprising a polypeptide having at least 70% sequence identity with an amino acid sequence selected from the group consisting of an amino acid sequence of SEQ ID NO:2, SEQ ID NO:3, or amino acid residues 2-50 of SEQ ID NO:2; and (b) detecting the presence of antibodies present in the test sample. More specifically, the present invention includes a method of detecting antibodies to *P. vivax* in a test sample comprising the steps of: (a) contacting the test sample suspected of containing the antibodies with a *P. vivax* protein or antigen comprising a polypeptide having at least 70% sequence identity with an amino acid sequence selected from the group consisting of an amino acid sequence of SEQ ID NO:2, SEQ ID NO:3, and amino acid residues 2-50 of SEQ ID NO:2, or fragment thereof, for a time and under conditions sufficient to allow the formation of antibody/antigen complexes; (b) adding a conjugate to the resulting antibody/antigen complexes for a time and under conditions sufficient to allow the conjugate to bind to the bound antibody, the conjugate comprising an antibody attached to a signal generating compound capable of generating a detectable signal; (c) detecting the presence of the antibody which can be present in the test sample by detecting the signal generated by the signal generating compound. A control or calibrator can also be used which binds to the antigen. The *P. vivax* antigen can comprise a polypeptide having at least 70% to 99%, such as 80%, 85%, 90%, 91%, 92%, 93%, 94%, 95%, 96%, 97%, 98% and 99% sequence identity to an amino acid sequence selected from the group consisting of an amino acid sequence of SEQ ID NO:2, SEQ ID NO:3, and amino acid residues 2-50 of SEQ ID NO:2, or fragment thereof. A fragment of these polypeptides can be approximately 8-56 amino acid residues, such as 8, 9, 10, 20, 30, 40, 50, 51, 52, 53, 54, 55, and 56 residues. The antigen can comprise a polypeptide consisting essentially of the amino acid sequences of SEQ ID NO:2, SEQ ID NO:3, or amino acid residues 2-50 of SEQ ID NO:2. Finally, the antigen can consist of the amino acid sequences of SEQ ID NO:2, SEQ ID NO:3, or amino acid residues 2-50 of SEQ ID NO:2.

In addition to the above-described assays in which one is detecting the presence of antibodies against one species of *Plasmodium* (e.g., *P. malariae* or *P. ovale*), one can also carry out assays that detect antibodies in a test sample against two or more species of *Plasmodium*. For example, one can wish to carry out an assay in which one can detect all known species of *Plasmodium* that infect humans, thereby eliminating the risk of false negative results obtained with existing assays. Thus, the present invention includes a method of detecting antibodies to *P. malariae, P. falciparum, P. vivax* and *P. ovale* in a test sample comprising the steps of: (a) contacting the test sample suspected of containing at least one of these four types of antibodies with: (1) an antigen of *P. malariae*; (2) an antigen of *P. ovale*; (3) an antigen of *P. falciparum* and (4) an antigen of *P. vivax* comprising a polypeptide having at least 70% sequence identity with an amino acid sequence selected from the group consisting of an amino acid sequence of SEQ ID NO:2, SEQ ID NO:3, or amino acid residues 2-50 of SEQ ID NO:2; and (b) detecting the presence of antibodies, to one or more of said antigens, present in the test sample, by detecting presence of complexes, for example. More specifically, the present invention includes a method of detecting antibodies to *P. malariae, P. ovale, P. vivax* and *P. falciparum* in a test sample comprising the steps of: (a) contacting the test sample with (1) an antigen of *P. malariae*; (2) an antigen of *P. ovale*; (3) an antigen of *P. falciparum* and (4) an antigen of *P. vivax* comprising a polypeptide having at least 70% sequence identity with an amino acid sequence selected from the group consisting of an amino acid sequence of SEQ ID NO:2, SEQ ID NO:3, or amino acid residues 2-50 of SEQ ID NO:2; (b) adding a conjugate to the resulting antibody/antigen complexes for a time and under conditions sufficient to allow each conjugate to bind to the bound antibody wherein said conjugate comprises an antibody attached to a signal generating compound capable of generating a detectable signal; and (c) detecting the presence of antibody which can be present in the test sample by detecting the signal generated by the signal generating compound. A control or calibrator can also be used which binds to the antigens. (The presence of the complexes indicates that at least one of the four types of antibodies is present in the test sample. In particular, the assay has the ability to detect the presence of all four types of antibodies in a sample thereby rendering the sample positive and preventing false negatives. One can not wish to know precisely which one or more of the antibody types is present (as when screening a suitable blood sample for donation purposes); however, as is described herein, such a determination is possible if desired). The *P. vivax* antigen can comprise a polypeptide having at least 70% to 99%, such as 80%, 85%, 90%, 91%, 92%, 93%, 94%, 95%, 96%, 97%, 98% and 99% sequence identity to an amino acid sequence selected from the group consisting of an amino acid sequence of SEQ ID NO:2, SEQ ID NO:3, and amino acid residues 2-50 of SEQ ID NO:2, or fragment thereof. A fragment of these polypeptides can be approximately 8-56 amino acid residues, such as 8, 9, 10, 20, 30, 40, 50, 51, 52, 53, 54, 55, and 56 residues. The antigen can comprise a polypeptide consisting essentially of the amino acid sequences of SEQ ID NO:2, SEQ ID NO:3, or amino acid residues 2-50 of SEQ ID NO:2. Finally, the antigen can consist of the amino acid sequences of SEQ ID NO:2, SEQ ID NO:3, or amino acid residues 2-50 of SEQ ID NO:2.

It should be noted that any previously described *P. falciparum, P. vivax, P. malariae* and *P. ovale* antigen or antigens can be utilized in combination with any one or more of the antigens of the present invention (e.g., Merozoite Surface Protein, Circumsporozoite Surface Protein Exported Protein 1, Apical Membrane Antigen, Cytoadherence-Linked Asexual Gene, Histidine-rich protein 2, FeSOD, pLDH and Erythrocyte binding antigen) with respect to the kits, vaccines and assays described herein.

Vaccines

The present invention also includes a vaccine comprising one or more of the polypeptides, or antigens thereof, as described herein. Such a vaccine is used for active immunization of a mammal, for example, a human who risks being exposed to one or more *Plasmodium* antigens (for example, due to travel within a region in which malaria is prevalent). For example, the vaccine can contain at least one antigen selected from the group consisting of: 1) a *P. vivax* antigen comprising a polypeptide having at least 70% sequence identity with an amino acid sequence selected from the group consisting of an amino acid sequence of SEQ ID NO:2, SEQ ID NO:3, or amino acid residues 2-50 of SEQ ID NO:2. The *P. vivax* antigen can comprise a polypeptide having at least 70% to 99%, such as 80%, 85%, 90%, 91%, 92%, 93%, 94%, 95%, 96%, 97%, 98% and 99% sequence identity to an amino acid sequence selected from the group consisting of an amino acid sequence of SEQ ID NO:2, SEQ ID NO:3, and amino acid residues 2-50 of SEQ ID NO:2, or fragment thereof. A fragment of these polypeptides can be approximately 8-56 amino acid residues, such as 8, 9, 10, 20, 30, 40, 50, 51, 52, 53, 54, 55, and 56 residues. The antigen can comprise a polypeptide consisting essentially of the amino acid sequences of SEQ ID NO:2, SEQ ID NO:3, or amino acid residues 2-50 of SEQ ID NO:2. Finally, the antigen can consist of the amino acid sequences of SEQ ID NO:2, SEQ ID NO:3, or amino acid residues 2-50 of SEQ ID NO:2.

Alternatively, if passive immunization is desired, one can administer one or more antibodies to the following antigens (as a vaccination): a polypeptide having at least 70% sequence identity with an amino acid sequence selected from the group consisting of an amino acid sequence of SEQ ID NO:2, SEQ ID NO:3, or amino acid residues 2-50 of SEQ ID NO:2. The *P. vivax* antigen can comprise a polypeptide having at least 70% to 99%, such as 80%, 85%, 90%, 91%, 92%, 93%, 94%, 95%, 96%, 97%, 98% and 99% sequence identity to an amino acid sequence selected from the group consisting of an amino acid sequence of SEQ ID NO:2, SEQ ID NO:3, and amino acid residues 2-50 of SEQ ID NO:2, or fragment thereof. A fragment of these polypeptides can be approximately 8-56 amino acid residues, such as 8, 9, 10, 20, 30, 40, 50, 51, 52, 53, 54, 55, and 56 residues. The antigen can comprise a polypeptide consisting essentially of the amino acid sequences of SEQ ID NO:2, SEQ ID NO:3, or amino acid residues 2-50 of SEQ ID NO:2. Finally, the antigen can consist of the amino acid sequences of SEQ ID NO:2, SEQ ID NO:3, or amino acid residues 2-50 of SEQ ID NO:2.

Diagnostic Kits

Diagnostic kits are also included within the scope of the present invention. The present invention includes kits for determining the presence of antibodies to *P. vivax* in a test sample. A kit can comprise: (a) a *P. vivax* antigen comprising a polypeptide having at least 70% sequence identity with an amino acid sequence selected from the group consisting of an amino acid sequence of SEQ ID NO:2, SEQ ID NO:3, or amino acid residues 2-50 of SEQ ID NO:2; and (b) a conjugate comprising an antibody attached to a signal-generating compound capable of generating a detectable signal. The kit can also contain a control or calibrator which comprises a reagent which binds to the antigen. The *P. vivax* antigen can comprise a polypeptide having at least 70% to 99%, such as 80%, 85%, 90%, 91%, 92%, 93%, 94%, 95%, 96%, 97%, 98% and 99% sequence identity to an amino acid sequence selected from the group consisting of an amino acid sequence of SEQ ID NO:2, SEQ ID NO:3, and amino acid residues 2-50 of SEQ ID NO:2, or fragment thereof. A fragment of these polypeptides can be approximately 8-56 amino acid residues, such as 8, 9, 10, 20, 30, 40, 50, 51, 52, 53, 54, 55, and 56 residues. The antigen can comprise a polypeptide consisting essentially of the amino acid sequences of SEQ ID NO:2, SEQ ID NO:3, or amino acid residues 2-50 of SEQ ID NO:2. Finally, the antigen can consist of the amino acid sequences of SEQ ID NO:2, SEQ ID NO:3, or amino acid residues 2-50 of SEQ ID NO:2.

The present invention also includes a kit for determining the presence of antibody to *P. vivax* in a test sample. A kit can comprise: (a) a *P. vivax* antigen comprising a polypeptide having at least 70% sequence identity with an amino acid sequence selected from the group consisting of an amino acid sequence of SEQ ID NO:2, SEQ ID NO:3, or amino acid residues 2-50 of SEQ ID NO:2; and (b) a conjugate comprising an antibody attached to a signal-generating compound capable of generating a detectable signal. The *P. vivax* antigen can comprise a polypeptide having at least 70% to 99%, such as 80%, 85%, 90%, 91%, 92%, 93%, 94%, 95%, 96%, 97%, 98% and 99% sequence identity to an amino acid sequence selected from the group consisting of an amino acid sequence of SEQ ID NO:2, SEQ ID NO:3, and amino acid residues 2-50 of SEQ ID NO:2, or fragment thereof. A fragment of these polypeptides can be approximately 8-56 amino acid residues, such as 8, 9, 10, 20, 30, 40, 50, 51, 52, 53, 54, 55, and 56 residues. The antigen can comprise a polypeptide consisting essentially of the amino acid sequences of SEQ ID NO:2, SEQ ID NO:3, or amino acid residues 2-50 of SEQ ID NO:2. Finally, the antigen can consist of the amino acid sequences of SEQ ID NO:2, SEQ ID NO:3, or amino acid residues 2-50 of SEQ ID NO:2.

Additionally, the present invention includes a kit for determining the presence of antibody to *P. malariae, P. ovale, P. vivax* and *P. falciparum*. Such a kit can comprise: (1) a *P. malariae* antigen; (2) a *P. ovale* antigen; (3) a *P. vivax* antigen as previously described; and (4) a *P. falciparum* antigen and (5) a conjugate comprising an antibody attached to a first signal generating compound capable of generating a detectable signal.

Ab Production

"Antibody" (Ab) comprises single Abs directed against a target antigen (an anti-target antigen Ab), anti-target antigen Ab compositions with poly-epitope specificity, single chain anti-target antigen Abs, and fragments of anti-target antigen Abs. A "monoclonal antibody" (mAb) is obtained from a population of substantially homogeneous Abs, i.e., the individual Abs comprising the population are identical except for possible naturally-occurring mutations that can be present in minor amounts. Exemplary Abs include polyclonal (pAb), monoclonal (mAb), humanized, bi-specific (bsAb), and heteroconjugate Abs.

Polyclonal Abs can be raised in a mammalian host by one or more injections of an immunogen and, if desired, an adjuvant. Typically, the immunogen (and adjuvant) is injected in the mammal by multiple subcutaneous or intraperitoneal injections. The immunogen can include a target antigen or a target antigen-fusion polypeptide. Examples of adjuvants include Freund's complete and monophosphoryl Lipid A synthetic-trehalose dicorynomycolate (MPL-TDM). To improve the immune response, an immunogen can be conjugated to a polypeptide that is immunogenic in the host, such as keyhole limpet hemocyanin (KLH), serum albumin, bovine thyroglobulin, and soybean trypsin inhibitor. Protocols for antibody production are well-known (Ausubel et al., 1987; Harlow and Lane, 1988; Harlow and Lane, 1999). Alternatively, pAbs can be made in chickens, producing IgY molecules (Schade et al., 1996).

Anti-target antigen mAbs can be prepared using hybridoma methods (Milstein and Cuello, 1983). Hybridoma methods consist of usually at least four steps: (1) immunizing a host, or lymphocytes from a host; (2) harvesting the mAb-secreting lymphocytes, (3) fusing the lymphocytes to immortalized cells, and (4) selecting those cells that secrete the desired (anti-target antigen) mAb.

A mouse, rat, guinea pig, hamster, or other appropriate host is immunized to elicit lymphocytes that produce or are capable of producing Abs that will specifically bind to the immunogen. Alternatively, lymphocytes can be immunized in vitro. If human cells are desired, peripheral blood lymphocytes (PBLs) can be used.

The lymphocytes are then fused with an immortalized cell line to form hybridoma cells, facilitated by a fusing agent such as polyethylene glycol (PEG) (Galfre et al., 1977; Goding, 1996). Rodent, bovine, or human myeloma cells immortalized by transformation can be used, or rat or mouse myeloma cell lines. Because pure populations of hybridoma cells and not unfused immortalized cells are desired, the cells after fusion are grown in a suitable medium that inhibits the growth or survival of unfused, immortalized cells. A common technique uses parental cells that lack the enzyme hypoxanthine guanine phosphoribosyl transferase (HGPRT or HPRT). In this case, hypoxanthine, aminopterin and thymidine are added to the medium (HAT medium) to prevent the growth of HGPRT-deficient cells while permitting hybridomas to grow.

Desirable immortalized cells fuse efficiently; can be isolated from mixed populations by selecting in a medium such as HAT; and support stable and high-level expression of antibody after fusion. Useful immortalized cell lines are murine myeloma lines, available from the American Type Culture Collection (Manassas, Va.). Human myeloma and mouse-human heteromyeloma cell lines also have been described for the production of human mAbs (Kozbor et al., 1984; Schook, 1987).

Because hybridoma cells secrete antibody extracellularly, the culture media can be assayed for the presence of mAbs directed against a target antigen. Immunoprecipitation or in vitro binding assays, such as radio immunoassay (RIA) or enzyme-linked immunoabsorbent assay (ELISA), can be used to measure the binding specificity of mAbs (Harlow and Lane, 1988; Harlow and Lane, 1999), including Scatchard analysis (Munson and Rodbard, 1980).

Anti-target antigen mAb secreting hybridoma cells can be isolated as single clones by limiting dilution procedures and sub-cultured (Goding, 1996). Suitable culture media include Dulbecco's Modified Eagle's Medium, RPMI-1640, or if desired, a protein-free, protein-reduced or serum-free medium (e.g., Ultra DOMA PF or HL-1; Biowhittaker; Walkersville, Md.). The hybridoma cells can also be grown in vivo as ascites.

The mAbs can be isolated or purified from the culture medium or ascites fluid by conventional Ig purification procedures such as polypeptide A-Sepharose, hydroxylapatite chromatography, gel electrophoresis, dialysis, ammonium sulfate precipitation or affinity chromatography (Harlow and Lane, 1988; Harlow and Lane, 1999).

Once antibodies have been produced that recognize a target antigen, the cells producing such antibodies, such as hybridomas, can be used as a basis to isolate the polynucleotide sequences encoding the antibodies. Once isolated, these sequences can be used to produce the antibodies in vitro, or to be manipulated to make, for example, chimeric antibodies.

The Abs can also be made by recombinant methods. DNA encoding anti-target antigen mAbs can be readily isolated and sequenced using conventional procedures, e.g., using oligonucleotide probes that specifically bind to murine heavy and light antibody chain genes, to probe DNA isolated from anti-target antigen mAb-secreting hybridoma cell lines. Once isolated, the isolated DNA fragments are sub-cloned into expression vectors that are then transfected into host cells such as simian COS-7 cells, CHO cells, or myeloma cells that do not otherwise produce Ig polypeptide, to express mAbs. The isolated DNA fragments can be modified by substituting the coding sequence for human heavy and light chain constant domains in place of the homologous murine sequences (Morrison et al., 1987), or by fusing the Ig coding sequence to all or part of the coding sequence for a non-Ig polypeptide. Such a non-Ig polypeptide can be substituted for the constant domains of an antibody, or can be substituted for the variable domains of one antigen-combining site to create a chimeric bivalent antibody.

Mammalian host cells for expressing the recombinant antibodies of the invention include CHO (CHO cells) (including dhfr-CHO cells (Urlaub and Chasin, 1980), used with a DHFR selectable marker, (Kaufman, 1990), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods.

In one system for recombinant expression of an antibody, or antigen-binding portion thereof, a recombinant expression vector encoding both the antibody heavy chain and the antibody light chain is introduced into dhfr-CHO cells by transfection. The recombinant expression vector carries a DHFR gene, which allows for selection of CHO cells that have been transfected with the vector. The selected transformant host cells are cultured to allow for expression of the antibody heavy and light chains, and intact antibody is recovered from the culture medium.

Monovalent Abs

Monovalent Abs do not cross-link each other. One method involves recombinant expression of Ig light chain and modified heavy chain. Heavy chain truncations generally at any point in the Fc region prevents heavy chain cross-linking. Alternatively, the relevant cysteine residues are substituted with another amino acid residue or are deleted, preventing crosslinking by disulfide binding. In vitro methods are also suitable for preparing monovalent Abs. Abs can be digested to produce fragments, such as Fab (Harlow and Lane, 1988; Harlow and Lane, 1999).

Humanized and Human Abs

Humanized forms of non-human Abs that bind a target antigen are chimeric Igs, Ig chains or fragments (such as Fv, Fab, Fab', F(ab')$_2$ or other antigen-binding subsequences of Abs) that contain minimal sequence derived from non-human Ig.

Generally, a humanized antibody has one or more amino acid residues introduced from a non-human source. These non-human amino acid residues are often referred to as "import" residues that are typically taken from an "import" variable domain. Humanization is accomplished by substituting rodent CDRs or CDR sequences for the corresponding sequences of a human antibody (Jones et al., 1986; Riechmann et al., 1988; Verhoeyen et al., 1988). Such "humanized" Abs are chimeric Abs, wherein substantially less than an intact human variable domain has been substituted by the corresponding sequence from a non-human species. In practice, humanized Abs are typically human Abs in which some CDR residues and possibly some FR residues are substituted by residues from analogous sites in rodent Abs. Humanized Abs include human Igs (recipient antibody) in which residues from a complementary determining region (CDR) of the recipient are replaced by residues from a CDR of a non-human species (donor antibody), such as mouse, rat or rabbit, having the desired specificity, affinity and capacity. In some instances, corresponding non-human residues replace Fv framework residues of the human Ig. Humanized Abs can include residues that are found neither in the recipient antibody nor in the imported CDR or framework sequences. In general, the humanized antibody contains substantially all of at least one, and typically two, variable domains, in which most if not all of the CDR regions correspond to those of a non-human Ig and most if not all of the FR regions are those of a human Ig consensus sequence. The humanized antibody optimally also comprises at least a portion of an Ig constant region (Fc), typically that of a human Ig (Jones et al., 1986; Riechmann et al., 1988; Verhoeyen et al., 1988).

Human Abs can also be produced using various techniques, including phage display libraries (Hoogenboom et al., 1991; Marks et al., 1991) and human mAbs (Boerner et al., 1991; Reisfeld and Sell, 1985). Introducing human Ig genes into transgenic animals in which the endogenous Ig genes have been partially or completely inactivated can be exploited to synthesize human Abs. Upon challenge, human antibody production is observed, which closely resembles that seen in humans in all respects, including gene rearrangement, assembly, and antibody repertoire (Fishwild et al., 1996; Lonberg and Huszar, 1995; Lonberg et al., 1994; Marks et al., 1992).

Bi-Specific mAbs

Bi-specific mAbs bind at least two different antigens. For example, a binding specificity is a target antigen; the other is for any antigen of choice.

The recombinant production of bi-specific Abs is often achieved by co-expressing two Ig heavy-chain/light-chain pairs, each having different specificities (Milstein and Cuello, 1983). The random assortment of these Ig heavy and light chains in the resulting hybridomas (quadromas) produce a potential mixture of ten different antibody molecules, of which only one has the desired bi-specific structure. The desired antibody can be purified using affinity chromatography or other techniques (Traunecker et al., 1991).

To manufacture a bi-specific antibody, variable domains with the desired antibody-antigen combining sites are fused to Ig constant domain sequences (Suresh et al., 1986). The fusion is usually with an Ig heavy-chain constant domain, comprising at least part of the hinge, CH2, and CH3 regions. The first heavy-chain constant region (CH1) containing the site necessary for light-chain binding is in at least one of the fusions. DNAs encoding the Ig heavy-chain fusions and, if desired, the Ig light chain, are inserted into separate expression vectors and are co-transfected into a suitable host organism.

The interface between a pair of antibody molecules can be engineered to maximize the percentage of heterodimers that are recovered from recombinant cell culture (Carter, 1986). In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This mechanism increases the yield of the heterodimer over unwanted end products, such as homodimers.

Bi-specific Abs can be prepared as full length Abs or antibody fragments (e.g., Fab'$_2$ bi-specific Abs). One technique to generate bi-specific Abs exploits chemical linkage. Intact Abs can be proteolytically cleaved to generate Fab'$_2$ fragments (Brennan et al., 1985). Fragments are reduced with a dithiol complexing agent, such as sodium arsenite, to stabilize vicinal dithiols and prevent intermolecular disulfide formation. The generated Fab' fragments are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bi-specific antibody.

Fab' fragments can be directly recovered from E. coli and chemically coupled to form bi-specific Abs. For example, fully humanized bi-specific Fab'$_2$ Abs can be produced (Shalaby et al., 1992). Each Fab' fragment is separately secreted from E. coli and directly coupled chemically in vitro, forming the bi-specific antibody.

Various techniques for making and isolating bi-specific antibody fragments directly from recombinant cell culture have also been described. For example, leucine zipper motifs can be exploited (Kostelny et al., 1992). Peptides from the Fos and Jun polypeptides are linked to the Fab' portions of two different Abs by gene fusion. The antibody homodimers are reduced at the hinge region to form monomers and then re-oxidized to form antibody heterodimers. This method can also produce antibody homodimers. "Diabody" technology provides an alternative method to generate bi-specific antibody fragments (Holliger et al., 1993). The fragments consist of a heavy-chain VH connected to a light-chain VL by a linker that is too short to allow pairing between the two domains on the same chain. The VH and VL domains of one fragment are forced to pair with the complementary VL and VH domains of another fragment, forming two antigen-binding sites. Another strategy for making bi-specific antibody fragments is the use of single-chain Fv (sFv) dimers (Gruber et al., 1994). Abs with more than two valencies can also be made, such as tri-specific Abs (Tutt et al., 1991). Exemplary bi-specific Abs can bind to two different epitopes on a given target antigen.

By way of example, and not of limitation, examples of the present invention shall now be given.

EXAMPLE 1

Design, Cloning and Expression of the Presumptive C-Terminal Domain of the P. Vivax EXP1 Gene Plasmodium vivax EXP1 Gene design. This example describes the design of synthetic Pv-EXP1 gene, encoding the C-terminal portion of the EXP1 protein, from P. vivax, which is optimized for expression in E. coli. Gene Designer software from DNA 2.0, Inc. (Menlo Park, Calif.) was used to design the gene sequence discussed below. The sequence of the encoded EXP1 protein for P. vivax was predicted based on sequence homology with the P. falciparum and P. yoelii proteins, and by identifying potential splice sites from the P. vivax genomic sequence. The nucleotide sequence for the optimized P. vivax EXP1 gene is shown in FIG. 1A (SEQ ID NO:1), and the encoded amino acid sequence is shown in FIG. 1B (SEQ ID NO:2). The gene contains a 5'-EcoRI site followed by a start codon, the body of the gene encoding the predicted C-terminal amino acid sequence of P. vivax EXP1, a sequence encoding a 6-histidine tag, a stop codon and a BamHI site. The restriction enzyme sites were used for cloning into expression vectors, and the 6-histidine tag was included to facilitate subsequent purification of the expressed protein.

Preparation of synthetic EXP1 gene from P. vivax. E. coli cells containing plasmid clone of the P. vivax synthetic EXP1 gene (GenScript Corp., (Piscataway, N.J.)) were grown, and the plasmid purified using the Wizard Plus SV Minipreps DNA Purification Kit (Promega, Madison, Wis.) according to the package insert. The plasmid was digested in a 50 µl reaction for 2 hours at 37° C. in the presence of 20 units of the restriction enzyme EcoRI, 20 units of the restriction enzyme BamHI and 1×EcoRI Buffer (New England Biolabs, Beverly, Mass.). The digests were electrophoresed on a 1.0% agarose TAE ethidium bromide gel to separate the insert from the vector. The approximately 185 base pair insert was then excised from the agarose gel, and the DNA was extracted from the agarose using the QIAEX II Agarose Gel Extraction Kit (Qiagen, Valencia, Calif.) according to the package insert.

Preparation of the CKS-fusion expression vector for cloning. E. coli cells containing the CKS-fusion expression vector pJO200 (Abbott Laboratories, Abbott Park, Ill.) were grown, and the plasmid purified using the Wizard Plus SV Minipreps DNA Purification Kit (Promega, Madison, Wis.) according to the package insert. The plasmid (10 µg) was digested in a 1500 µl reaction for 2.5 hrs. at 37° C. in the presence of 200 units of the restriction enzyme EcoRI, 200 units of the restriction enzyme BamHI and 1×EcoRI Buffer (New England Biolabs, Beverly, Mass.). The digests were electrophoresed on a 1.0% agarose TAE ethidium bromide gel to separate the insert from the vector. Linearized vector was then excised from the agarose gel, and the DNA was extracted from the agarose using the QIAEX II Agarose Gel Extraction Kit (Qiagen, Valencia, Calif.) according to the package insert.

Cloning of the EXP1 insert into the CKS-fusion expression vector. A portion (2 μl) of the purified EcoRI/BamHI digested EXP1 insert (see above) was added to a ligation reaction (10 μl) containing EcoRI/BamHI digested expression vector pJO200 (~0.6 μg, see above), 1×T4 DNA Ligase Buffer and 400 units T4 DNA Ligase (New England Biolabs, Beverly, Mass.). The ligation reactions were incubated overnight at 16° C. then transformed into E. coli TOP10 competent cells (Stratagene, La Jolla, Calif.) according to the package insert. Plasmids were purified from the TOP10 clones as described above and transformed into competent cells of the protease deficient E. coli strain BL21 (Novagen, Madison, Wis.) according to the package insert.

Expression and purification of EXP1 recombinant protein. BL21 cells containing the EXP1 expression plasmid (See the description above) were grown in 100 ml culture at 37° C. until an $OD_{595}$ of approximately 0.8 was reached, at which time IPTG was added to a final concentration of 1 mM to induce expression. After 3 hours of induction at 37° C., the cells were harvested by centrifugation and the pelleted cells were lysed with BugBuster Extraction Reagent (Novagen, Madison, Wis.) according to the package insert. The expressed EXP1 present in the soluble fraction of the lysate was purified using a His•Bind Purification Kit (Novagen, Madison, Wis.) according to the package insert. The purified recombinant protein was dialyzed into 0.01 M phosphate buffer, pH 7.4 containing 0.15 M NaCl (PBS) prior to quantitation.

EXAMPLE 2

Design of P. Vivax EXP1 Synthetic Peptide

This example describes the design of the synthetic Pv-EXP1 peptide constituting the C-terminal portion of the EXP1 protein, from P. vivax. The predicted amino acid sequence of the Pv-EXP1 protein was based on sequence homology with the P. falciparum and P. yoelii proteins, and by identifying potential splice sites within the putative EXP1 gene from the P. vivax genomic sequence. The Pv-EXP1 peptide was synthesized by the GenScript Corp. (Piscataway, N.J.) with a biotin label at the N-terminus. The Pv-EXP1 peptide sequence (See, FIG. 1C (SEQ ID NO:3)) comprises the putative C-terminal domain of EXP1 downstream of the transmembrane anchor.

EXAMPLE 3

P. Vivax EXP1 Immunoassay Using Polystyrene Beads

P. vivax EXP1 CKS fusion protein was tested for its ability to detect IgG and/or IgM antibodies by using a polystyrene bead assay. Several panels of human sera were tested including experimentally infected chimpanzees, normal blood donors, and malaria patients.

The panels represent populations wherein the time between onset of illness (i.e., clinical diagnosis) or infection and sample collection increases from days or weeks (experimentally infected chimps, Indian malaria patients, and American malaria patients) to years (American blood donors with history of past malaria).

The data suggest that P. vivax EXP1 antibodies are most frequently detected early after infection or disease onset (days to months) but are undetected after one or more years following malaria illness. Hence, P. vivax EXP1 appears to be a marker of recent rather than past infection.

Coating of polystyrene beads. One quarter-inch polystyrene beads were used as the solid phase for the peptide EIAs. Prior to coating, beads were washed with 15% 1-propanol (in water) at room temperature for 20 minutes without agitation. 1-Propanol was removed, and the beads were rinsed twice with deionized water. The washed beads were then added to a vial containing recombinant antigen diluted to 0.25-5 μg/mL in 0.1 M sodium phosphate, pH 7.0 (0.233 ml per bead). Beads were incubated at 40° C. for 2 hours with gentle mixing. Beads were then washed three times with PBS and then incubated in PBS containing 0.1% Triton X-100 at 40° C. for 1 hour with gentle mixing. They were again washed three times in PBS and then incubated at 40° C. in 5% BSA in PBS for 1 hour with gentle mixing. Beads were washed four times with PBS and then incubated at room temperature in PBS containing 5% sucrose without mixing for 20 minutes. Sucrose buffer was removed and beads air-dried. Coated beads were stored desiccated at 4° C.

Immunoassay Method. Serum and plasma were tested for their immunoreactivity to antigen coated polystyrene beads. Specimens were diluted 1:16 in diluent buffer (Tris-phosphate buffer pH 7.8 comprising 20% goat serum, 10% calf serum, 0.2% Triton X-100 and sodium azide), and 0.010 ml was added to a well of a plastic test tray and then combined with an additional 0.20 mL of the same diluent buffer for a final sample dilution of 1:336. The recombinant protein coated bead was added to the diluted sample and incubated at 37° C. for 90 minutes with mixing. Beads were then washed with 11-14 mL of deionized water followed by the addition of 0.2 ml of peroxidase-labeled goat anti-human IgG (0.02 microgram per mL) or anti-human IgM. Beads were incubated at 37° C. for 30 minutes with mixing. Beads were washed with 11-14 mL deionized water and then transferred into plastic tubes to which 0.3 ml of OPD (0.3% O-phenylenediamine-2-HCl in citrate buffer containing 0.02% $H_2O_2$) substrate was added and incubated in the dark at room temperature for 30 min without mixing. Reactions were quenched by the addition of 1 ml of 1N $H_2SO_4$ and the optical density (OD) at 492 nm determined. The OD is directly proportional to the amount of antibody bound to the bead. Signal to negative (S/N) ratios are calculated for each test sample by dividing the test sample OD by the mean negative control OD. Specimens with S/N values greater-than or equal-to 5.00 (provisional cutoff value) were assumed to be immunoreactive.

P. vivax EXP1 Antibody Assay optimization. CKS-Pv-EXP1 fusion protein was coated onto polystyrene beads using a variety of conditions in order to determine conditions for optimal assay sensitivity. Beads were then tested for immunoreactivity using human sera from individuals with blood smear diagnosed plasmodium infection. Immunoassay conditions were as described above except where noted. The coating concentration of CKS-Pv-EXP1 antigen was 2.0 ug/mL. CKS-Pv-EXP1 immunoreactivity was compared to that of CKS-Pv-MSP1-19 and to test results obtained using a commercial plasmodium antibody assay.

| Assay Condition | Polystyrene bead coating conditions | Assay Diluents |
|---|---|---|
| 1 | 0.1M NaPO4 (pH 7.2), 40° C., X mM DTT | HCV 2.0 EIA |
| 2 | 0.1M NaPO4 (pH 7.2), 40° C. | HCV 2.0 EIA |
| 3 | 50 mM MES (pH 6.3), 40° C., X mM DTT | HCV 2.0 EIA |
| 4 | 50 mM MES (pH 6.3), 40° C. | HCV 2.0 EIA |
| 5 | 50 mM MES (pH 6.3), 40° C. | HTLV EIA |
| 7 | 0.1M NaPO4 (pH 7.2), 56° C., X mM DTT | HCV 2.0 EIA |
| 8 | 0.1M NaPO4 (pH 7.2), 56° C. | HCV 2.0 EIA |
| 9 | 50 mM MES (pH 6.3), 56° C., X mM DTT | HCV 2.0 EIA |
| 10 | 50 mM MES (pH 6.3), 56° C. | HCV 2.0 EIA |

Effect of assay condition on background $OD_{492}$ nm values. The highest OD values were obtained using condition 7 and 8 as shown below in Table 1 while the lowest were observed using condition 5. The addition of DTT to coating buffers did not improve background and in some cases (specifically compared to conditions 9 to 10) increased background. Coating at 56° C. in any of the buffers increased background readings.

TABLE 1

| | Assay Condition and OD 492 nm | | | | | | | | |
|---|---|---|---|---|---|---|---|---|---|
| Sample | 1 | 2 | 3 | 4 | 5 | 7 | 8 | 9 | 10 |
| NHP | 0.094 | 0.099 | 0.036 | 0.028 | 0.025 | 0.136 | 0.123 | 0.058 | 0.037 |
| NHP | 0.085 | 0.094 | 0.027 | 0.026 | 0.020 | 0.155 | 0.108 | 0.043 | 0.038 |
| NHP | 0.088 | 0.088 | 0.042 | 0.028 | 0.022 | 0.131 | 0.112 | 0.041 | 0.037 |
| NHP | 0.089 | 0.065 | 0.040 | 0.025 | 0.020 | 0.158 | 0.123 | 0.043 | 0.035 |

NHP: normal human plasma

Effect of assay condition on sensitivity. Serum specimens collected from Indian malaria patients (*Plasmodium* infection confirmed by blood smear microscopy) were tested for presence of CKS-Pv-EXP1 IgG. Specimens were also tested for CKS-Pv-MSP1-19 IgG. All specimens had been previously tested for *Plasmodium* antibodies by using a commercial assay that detected IgG, IgM and/or IgA directed against *P. vivax* and *P. falciparum* antigens.

Assay conditions 4 and 5 shown in Table 2 below provided highest S/N ratios (and lowest background readings as shown above) and detected the most Pv-MSP1-19 IgG positive samples. S/N ratios using condition 4 had slightly higher S/N ratios than condition 5.

TABLE 2

| | | | | Assay condition and S/N ratio | | | | | | | |
|---|---|---|---|---|---|---|---|---|---|---|---|
| | | | | Antigen on bead | | | | | | | |
| | | | MSP1-19 | CKS-Pv-EXP1 | | | | | | | |
| | Infection | Commercial | | | | | | | | | |
| Sample | (blood smear) | ELISA S/CO | 2 | 1 | 2 | 3 | 4 | 5 | 7 | 8 | 9 | 10 |
| M022 | vivax | 24.54 | 196.1 | 1.0 | 0.9 | 0.7 | 1.0 | 1.5 | 0.8 | 0.6 | 0.9 | 0.7 |
| M029 | Pf & Pv | 24.54 | 124.5 | 2.0 | 2.7 | 3.2 | 5.2 | 3.5 | 1.6 | 1.9 | 3.1 | 3.4 |
| M034 | vivax | 24.54 | 196.7 | 1.1 | 1.4 | 1.3 | 1.7 | 1.1 | 1.0 | 1.2 | 1.3 | nd |
| M039 | vivax | 24.54 | 72.1 | 1.2 | 1.4 | 1.6 | 2.1 | 1.7 | 0.9 | 1.3 | 1.2 | nd |
| M045 | vivax | 24.54 | 6.1 | 1.1 | 1.1 | 1.0 | 1.0 | 1.1 | 0.8 | 0.8 | 1.0 | 0.8 |
| M085 | vivax | 19.20 | 157.9 | 15.9 | 22.5 | 36.8 | 56.7 | 64.1 | 11.0 | 14.2 | 27.4 | 40.6 |
| M107 | vivax | 19.20 | 196.7 | 13.5 | 21.5 | 36.4 | 69.3 | 52.0 | 10.1 | 13.6 | 31.3 | 46.9 |
| M113 | vivax | 19.20 | 1.3 | 0.6 | 0.9 | 0.7 | 1.4 | 1.1 | 0.6 | 0.9 | 0.6 | 0.7 |
| M146 | vivax | 19.20 | 157.9 | 22.5 | 23.1 | 50.1 | 74.8 | 54.1 | 13.8 | 17.2 | 40.0 | 54.4 |
| M102 | vivax | 18.93 | 196.7 | 12.3 | 15.5 | 27.5 | 43.7 | 33.8 | 7.9 | 11.3 | 22.1 | 33.6 |
| M106 | falicip | 18.93 | 48.2 | 1.1 | 1.4 | 1.1 | 1.6 | 1.9 | 0.9 | 1.0 | 1.1 | 1.0 |
| M060 | vivax | 18.16 | 196.7 | 11.7 | 13.3 | 22.5 | 40.4 | 38.3 | 7.9 | 10.3 | 17.0 | 29.0 |
| M101 | falicip | 17.47 | 11.9 | 1.1 | 1.2 | 1.5 | 1.8 | 2.3 | 1.0 | 1.2 | 1.3 | 1.7 |
| M041 | vivax | 17.05 | 196.7 | 6.0 | 6.6 | 11.2 | 17.6 | 14.1 | 3.9 | 4.8 | 9.9 | 14.6 |
| M049 | vivax | 7.61 | 2.2 | 0.9 | 0.8 | 0.3 | 0.6 | 0.7 | 0.7 | 0.9 | 0.5 | nd |
| M040 | vivax | 6.39 | 63.3 | 1.6 | 2.7 | 2.1 | 4.2 | 7.2 | 1.1 | 1.7 | 2.3 | 3.0 |
| M081 | falicip | 6.09 | 1.0 | 0.8 | 1.1 | 0.8 | 1.1 | 0.9 | 0.8 | 1.2 | 1.0 | 0.9 |
| M063 | vivax | 5.61 | 4.2 | 1.1 | 1.1 | 0.9 | 0.8 | 1.1 | 0.9 | 0.9 | 0.9 | 0.8 |
| M065 | vivax | 4.70 | 2.8 | 1.0 | 1.2 | 1.1 | 1.3 | 0.9 | 0.8 | 1.1 | 1.0 | 1.0 |
| M002 | vivax | 2.93 | 3.2 | 0.8 | 0.7 | 0.6 | 0.7 | 0.5 | 0.7 | 0.9 | 0.6 | 0.7 |
| M046 | falicip | 2.41 | 0.8 | 0.7 | 1.0 | 0.5 | 0.6 | 0.6 | 0.8 | 0.8 | 0.7 | 0.5 |
| M080 | falicip | 2.19 | 1.8 | 0.9 | 1.1 | 1.0 | 1.2 | 1.0 | 0.9 | 0.8 | 1.0 | 0.9 |
| M042 | vivax | 1.95 | 4.4 | 1.2 | 1.1 | 1.2 | 1.5 | 1.7 | 0.8 | 1.2 | 1.2 | 1.3 |
| M023 | vivax | 0.37 | 0.7 | 0.9 | 0.9 | 0.6 | 0.7 | 0.7 | 0.7 | 0.9 | 0.9 | 0.9 |
| M094 | falicip | 0.34 | 0.9 | 0.8 | 0.7 | 0.7 | 0.9 | 0.6 | 0.8 | 0.8 | 1.0 | 0.5 |
| no. S/N >= 5.00 | | | 14 | 6 | 6 | 6 | 7 | 7 | 5 | 5 | 6 | 6 | nd: not done.

EXAMPLE 4

Pv-EXP1 IgG Antibodies in Blood Donors with Previous Malaria

Blood donors in the United States must complete a questionnaire prior to donation. Donors who have had malaria are not permitted to donate for three years after they become free of symptoms. Travelers to malaria endemic regions are not permitted to donate blood for one year after leaving the area, provided they have not had symptoms of malaria. Immigrants from or residents of countries where malaria is common are not permitted to donate for three years after their departure from that country.

Plasma specimens were available from several donors who had disclosed previous malaria illness. These donor specimens were tested for the presence of IgG antibodies directed against MSP1-19 antigens from *P. malariae, P. ovale, P. falciparum* and *P. vivax* using individual antigens coated onto quarter-inch polystyrene beads. The donors were also tested for the presence of IgG antibodies directed to *P. vivax* EXP1 recombinant antigen. All specimens tested positive for *plasmodium* antibodies by using a commercial assay that detects IgG, IgM and/or IgA directed against *P. vivax* and *P. falciparum* antigens. Immunoassay results are shown in Table 3 below. Of the 14 commercial EIA antibody positive donors, 9 were positive for Pv-MSP1-19 antibodies and 4 were Pf-MSP1-19 IgG reactive. Of the Pv-MSP1-19 immunoreactive specimens none were reactive in the Pv-EXP1 EIA. The most recently reported malaria illness within the cohort occurred in 2006 (samples were collected in 2007) and the oldest malaria illness occurred in 1970. Thus, while Pv-MSP1-19 detected antibodies among donors whose malaria illness occurred as long ago as 1970 (37 years prior to blood donation) while Pv-EXP1 antibodies were undetected even among donors with malaria as recent as 2006.

risk of malaria varies depending on rainfall. During periods of epidemics or outbreaks, multiple infectious bites per person are possible.

Serum specimens were obtained from *plasmodium*-infected individuals from India with past or recent malaria. The infecting *plasmodium* species was identified by microscopic examination of blood smear at the time of sample collection. Some individuals were diagnosed by microscopy as dual infections. Specimens were tested for the presence of *plasmodium* antibodies by using a commercial assay that detects IgG, IgM and/or IgA directed against *P. vivax* and *P. falciparum* antigens. The results are shown in Table 4 below. Pv-MSP1-19 IgG antibodies were detected in all 27 (100%) individuals while 13/27 (48%) were Pv-EXP1 antibody positive. Among the 19 individuals with microscopy confirmed *P. vivax* infection, 19 (100%) were Pv-MSP1-19 IgG positive while only 11/19 (58%) were Pv-EXP1 IgG positive.

TABLE 4

| Sample ID | Plasmodium infection | Onset to Draw Interval (d) | Commercial EIA, S/CO | Pv-MSP1-19, S/N | Pv-EXP1, S/N |
|---|---|---|---|---|---|
| M034 | Pv | 30-60 | 24.5 | 196.7 | 1.5 |
| M041 | Pv | unknown | 17.1 | 196.7 | 17.1 |
| M043 | Pv | 10 | 24.5 | 196.7 | 71.1 |
| M050 | Pf, Pv | 9 | 24.5 | 196.7 | 6.7 |
| M060 | Pv | 30-60 | 18.2 | 196.7 | 29.2 |
| M102 | Pv | 3 | 18.9 | 196.7 | 38.3 |
| M107 | Pv | 3 | 19.2 | 196.7 | 78.3 |
| M022 | Pv | 30-60 | 24.5 | 196.1 | 0.8 |
| M109 | Pf | 4 | 18.9 | 170.5 | 0.5 |
| M104 | Pf | 2 | 18.9 | 166.5 | 14.5 |
| M004 | Pf | unknown | 19.2 | 157.9 | 1.1 |
| M085 | Pv | unknown | 19.2 | 157.9 | 49.1 |
| M146 | Pv | unknown | 19.2 | 157.9 | 67.2 |
| M029 | Pf, Pv | 30-60 | 24.5 | 124.5 | 6.4 |
| M121 | Pv | unknown | 19.2 | 119.4 | 6.4 |

TABLE 3

| | | | Commercial | EIA Reactivity, S/N values | | | |
|---|---|---|---|---|---|---|---|
| Donor No. | Donor Status | Malaria year | EIA, S/CO | Pf-MSP1-19 | Pv-MSP1-19 | Pv-EXP1 | Pm-MSP1-19 | Po-MSP1-19 |
| 8 | DEFERRED | 1985 | 20.25 | 0.9 | 31.0 | 1.1 | 0.8 | 0.5 |
| 14 | DEFERRED | 1995 | 20.25 | 0.7 | 21.1 | 1.0 | 0.7 | 0.7 |
| 27 | DEFERRED | 2006 | 20.25 | 1.1 | 95.2 | 2.0 | 0.7 | 0.7 |
| 42 | DEFERRED | 1970 | 20.25 | 0.9 | 27.2 | 0.9 | 0.7 | 0.4 |
| 11 | DEFERRED | 1997 | 15.90 | 0.9 | 7.1 | 0.9 | 0.6 | 0.3 |
| 46 | DEFERRED | 1995 | 14.03 | 12.5 | 14.8 | 3.0 | 0.8 | 1.1 |
| 36 | DEFERRED | 1994 | 13.23 | 0.9 | 30.0 | 2.2 | 0.7 | 0.7 |
| 38 | DEFERRED | 1995 | 13.06 | 2.8 | 51.1 | 1.8 | 0.9 | 0.5 |
| 58 | NON-DEFERRED | unknown | 11.46 | 22.1 | 0.4 | 0.5 | 1.2 | 0.7 |
| 1 | DEFERRED | 1997 | 10.53 | 2.5 | 5.9 | 0.9 | 1.0 | 0.7 |
| 51 | NON-DEFERRED | 1968 | 9.51 | 30.2 | 0.6 | 2.8 | 0.8 | 0.3 |
| 73 | NON-DEFERRED | 2004 | 5.70 | 0.7 | 4.0 | 1.0 | 0.6 | 0.4 |
| 43 | DEFERRED | 1970 | 3.45 | 6.9 | 1.8 | 1.5 | 0.7 | 0.3 |
| 33 | DEFERRED | 1980 | 2.50 | 2.7 | 4.7 | 0.9 | 0.9 | 0.4 |

EXAMPLE 5

Pv-EXP1 IgG Antibodies Among Malaria Patients from India

Malaria is endemic in most portions of India with approximately 95% of the population at risk for infection by *plasmodium* species that cause disease. In India, *P. falciparum* and *P. vivax* are most common with *P. malaria* representing a small number of cases and *P. ovale* being virtually nonexistent. In most areas of the country, incidence of malaria is low but the

TABLE 4-continued

| Sample ID | Plasmodium infection | Onset to Draw Interval (d) | Commercial EIA, S/CO | Pv-MSP1-19, S/N | Pv-EXP1, S/N |
|---|---|---|---|---|---|
| M048 | Pf | 10 | 24.5 | 99.4 | 8.5 |
| M135 | Pf, Pm | unknown | 19.2 | 82.4 | 2.3 |
| M039 | Pv | 6 | 24.5 | 72.1 | 1.6 |
| M044 | Pv | 11 | 24.5 | 65.3 | 6.0 |
| M040 | Pv | 3 | 6.4 | 63.3 | 2.5 |
| M106 | Pf | 3 | 18.9 | 48.2 | 1.4 |
| M001 | Pv | unknown | 19.2 | 38.3 | 2.2 |

TABLE 4-continued

| Sample ID | Plasmodium infection | Onset to Draw Interval (d) | Commercial EIA, S/CO | Pv-MSP1-19, S/N | Pv-EXP1, S/N |
|---|---|---|---|---|---|
| M093 | Pf | unknown | 18.9 | 24.9 | 0.8 |
| M110 | Pf | 4 | 7.5 | 12.7 | 0.7 |
| M101 | Pf | 3 | 17.5 | 11.9 | 2.1 |
| M082 | Pf | unknown | 18.9 | 8.3 | 2.5 |
| M036 | Pv | 30-60 | 24.5 | 6.7 | 0.9 |
| M045 | Pv | 10 | 24.5 | 6.1 | 1.1 |
| M047 | Pv | 8 | 24.5 | 5.9 | 1.0 |

EXAMPLE 6

Pv-EXP1 IgG Antibodies Among Malaria Patients from the USA

Human serum samples from individuals infected with *P. vivax* were obtained from Marianna Wilson, Chief, Reference Immunodiagnostic Laboratory, Centers for Disease Control and Prevention, Atlanta, Ga., USA (CDC). Immunofluorescent antibody titers for each human infective *plasmodium* species for each sample was provided, as was the *plasmodium* species identification determined by blood smear. All samples were collected prior to 1990 and are considered "anonymized residual human specimens" since original records regarding the identity of the donor/patient no longer exist. The time between infection or clinical presentation and samples collection is not known. However, it could be assumed that the specimens were collected soon after onset of symptoms since (a) samples were referred to the CDC Diagnostic Reference Laboratory for testing/confirmation and (b) *plasmodium* parasites were observed in the blood.

Sera from individuals with *P. vivax* infection were tested for anti-MSP1-19 (all species) and anti-Pv-EXP1 reactivity using bead EIAs (See, Table 5 below). *P. vivax* MSP1-19 IgG was detected in 8/8 individuals while *P. vivax* EXP1 IgG was detected in 6/8 (75%).

TABLE 5

| Sample | Species-specific IgG by IFA | Commercial EIA, S/CO | Pv-EXP1 | MSP1-19 EIAs | | | |
|---|---|---|---|---|---|---|---|
| | | | | Pv | Pf | Pm | Po |
| Pv-1 | Pv | 2.41 | 3.8 | 62.1 | 1.3 | 12.3 | 1.1 |
| Pv-2 | Pv | 19.20 | 102.6 | 67.4 | 1.3 | 2.7 | 8.3 |
| Pv-5 | Pv, Po | 19.20 | 102.6 | 67.4 | 1.3 | 2.0 | 11.0 |

TABLE 5-continued

| Sample | Species-specific IgG by IFA | Commercial EIA, S/CO | Pv-EXP1 | MSP1-19 EIAs | | | |
|---|---|---|---|---|---|---|---|
| | | | | Pv | Pf | Pm | Po |
| Pv-9 | Pv, Po | 19.20 | 102.6 | 67.4 | 0.6 | 2.5 | 13.2 |
| Pv-10 | Pv | 4.82 | 5.3 | 49.5 | 1.7 | 10.9 | 1.9 |
| Pv-11 | Pv, Po | 19.20 | 88.0 | 67.4 | 10.6 | 1.6 | 1.0 |
| Pv-12 | Pv | 6.69 | 5.0 | 41.0 | 0.5 | 0.9 | 1.4 |
| Pv-14 | Pv, Pf | 19.20 | 4.3 | 67.4 | 11.4 | 0.8 | 2.4 |

EXAMPLE 7

*Plasmodium Vivax* EXP1 and MSP1-19 Antibodies Among Experimentally Infected Chimpanzees Serum specimens were collected approximately 3-4 weeks post-infection from chimpanzees experimentally infected with *Plasmodium vivax*. All nine animals had readily detectable *P. vivax* IgG as determined by IFA. *P. vivax* infection was confirmed by microscopic examination of whole blood smears. These specimens were tested for *P. vivax* MSP1-19 and EXP1 IgG and IgM antibodies using bead EIAs. Results are shown in Table 6 with reactivity expressed as S/N ratio (provisional cutoff for positive result set at S/N of 5.00).

MSP1-19 IgG was detected in 7 of 9 animals while MSP1-19 IgM was detected an all 9. Using a recombinant-based EIA, EXP1 IgG was detected in 7 of 9 chimpanzees while an EXP1 peptide-based assay detected IgG in 4 of 9. The recombinant-based EXP1 assay detected IgM antibodies in 8 of the 9 animals.

TABLE 6

| | Species-specific IgG titer by IFA | | | | Pv-MSP1-19 | | Pv-EXP1 antigen | | |
|---|---|---|---|---|---|---|---|---|---|
| Animal ID | Pf | Pv | Pm | Po | IgG | IgM | IgG | IgM | peptide IgG |
| Amanda | 256 | ≧16384 | 256 | ≧16384 | 25.2 | 107.1 | 49.8 | 40.4 | 5.6 |
| Arthur | 4096 | ≧16384 | 1024 | ≧16384 | 44.9 | 107.1 | 188.1 | 40.4 | 35.1 |
| Brandy | 64 | ≧16384 | 16 | ≧16384 | 1.0 | 16.7 | 3.0 | 1.0 | 0.7 |
| Brodie | 64 | ≧16384 | 64 | ≧16384 | 19.1 | 107.1 | 8.3 | 39.8 | 1.1 |
| Callie | 256 | ≧16384 | 64 | ≧16384 | 14.5 | 107.1 | 117.0 | 18.1 | 6.0 |
| Edwina | 256 | 4096 | 64 | ≧16384 | 3.1 | 103.0 | 3.1 | 9.1 | 1.4 |
| Luther | 64 | 4096 | 64 | 256 | 12.8 | 107.1 | 12.0 | 40.4 | 2.0 |
| Mary | 4096 | ≧16384 | 1024 | ≧16384 | 107.1 | 107.1 | 31.4 | 35.9 | 2.8 |
| Patrick | 4096 | ≧16384 | 1024 | ≧16384 | 34.2 | 107.1 | 85.1 | 40.4 | 8.7 |

EXAMPLE 8

Reagents for Microparticle-Based Immunoassay

Preparation of Microparticles. Microparticles were coated with recombinant antigens cloned from the EXP1 regions of *Plasmodium vivax* (Pv-EXP1). See Example 1 for the preparation of recombinant protein. Microparticles coated with the recombinant PvEXP1 protein were prepared in the following manner. Briefly, a 250 µl aliquot of microparticles (4% weight/volume, 3.2 micron diameter (Interfacial Dynamics Corp., Portland, Oreg.) was mixed with 1.25 ml of a coating buffer (2-(N-Morpholino)ethanesulfonic acid (MES) buffer, pH 6.0) and pelleted in a microfuge for 2 minutes at 14,000×g. The particles were resuspended in 0.5 ml of the MES coating buffer, and 100 µg of the recombinant protein was added. (In this example, PvEXP1 solution: 9.1 µl for a final concentration of 0.20 mg/ml). The microparticle/protein solution was mixed and tumbled for 16 hours at room temperature. The microparticles were pelleted at 14,000×g for 2 minutes, and the solution was removed. The particles were resuspended in 1 ml phosphate buffered saline (pH 7.2) (PBS) and repelleted. The particles were washed with PBS twice more, then resuspended in 1 ml Microparticle Diluent (phosphate buffered saline (pH 6.5) with 11.5% sucrose). The microparticle concentration was determined by absorbance at 700 nm compared to a standard curve prepared from known concentrations of microparticles. The microparticle solution was diluted to a final concentration of 0.05% in Microparticle Diluent.

Preparation of Acridinium-Labeled Conjugates. For the antibody assay, mouse anti-human IgG directly labeled with acridinium can be prepared as follows: 53.6 µl of conjugation buffer (CB) containing sodium phosphate, NaCl, 3-(3-chlolamidopropyl)-dimethylammonio-1-propane-sulfonate (CHAPS, Sigma Chemical Company, Saint Louis, Mo.), pH 8.0 and 7.2 µl of N-hydroxysuccinimide ester of 10-(3-sulfopropyl)-N-tosyl-N-(2-carboxyethyl)-9-acridinium carboxamide (4 mg/ml in dimethyl formamide) was added to 131 µl of Mouse anti-Human IgG (4.59 mg/ml) and 601 µl of PBS at room temperature. The reaction mixture was mixed with a rotator for 20 minutes at room temperature. The reaction was quenched by loading the reaction mixture onto the HPLC. This was applied to a 300×7.8 mm Bio-Sil SEC-250 gel filtration column (Bio-Rad, Richmond, Calif.) which had been equilibrated with buffer containing CHAPS, NaCl and sodium phosphate, pH 6.3. The column was eluted at 1.0 ml/minute with the same buffer using a Beckman 421A controller equipped with a model 114M pump. Fractions of 1 ml were collected and the absorbance determined at 280 nm and 370 nm with a Beckman DU-7 spectrophotometer. The extent of acridinium incorporation was calculated using the methods as described in U.S. Pat. No. 5,705,330. The acridinium to IgG ratio (mole/mole) obtained was approximately 2.5. The conjugate was stored at 4° C.

EXAMPLE 9

PRISM Anti-Pv-EXP1 Assay

The PRISM™ antibody assay is described in U.S. Pat. No. 5,705,330, incorporated herein by reference, and the PRISM™ antigen and antibody assays are described in Shah and Stewart, The Immunoassay Handbook, second edition, edited by David Wild, p 297-303 (2001), also incorporated herein by reference. With respect to the present invention, the following procedures were utilized. The assay format is provided in FIG. 2. Generally, at station 1, 50 µl of control or sample, 50 µl of specimen diluent buffer (SDB, borate buffer, pH 7.5 containing TWEEN™ 20, TRITON™ X-100, urea, bovine serum albumin, newborn calf serum, NaCl, *E. coli* lysate and azide), and 50 µl of recombinant antigen coated microparticles (prepared as described in Example 7 above) were dispensed into each incubation well and assay timing was started. These were mixed by mutual diffusion of each into the other without external agitation or shaking to form a reaction mixture. At station 4, the reaction mixture was transferred to a detection well that contained a fibrous matrix and washed twice with 300 µl of transfer wash (TW, containing borate buffer, pH 7.0, with NaCl, TWEEN™ 20, Glycerol, urea, and PROCLIN® 300). After 18 minutes of incubation at 37° C., 50 µl of acridinium labeled mouse anti-human antibody was dispensed into the matrix of the detection well at station 5. The well was incubated for 23 minutes at 37° C., and the fibrous matrix containing the reaction mixture was washed three times with 100 µl of Final Wash (FW), containing tris buffer, pH 9.0, with LiCl, lithium dodecyl sulfate, polyethylene glycol 1500 and PROCLIN® 300 at station 8. At station 9, a chemiluminescence (CL) signal was generated by addition of an alkaline hydrogen peroxide solution, and the photons were measured by a photo multiplier tube. The amount of light emitted is proportional to the amount of antibody in the sample. The presence or absence of antibody in the sample is determined by comparing the number of photons collected from the sample to a negative (S/N) value. The results are expressed as S/N (signal to negative) in Table 7 below for a set of samples from acute and chronic infections. Samples which have an S/N greater than 5.0 are considered to be reactive for the antigen. The results are compared to results obtained from a commercially available enzyme-linked immunoassay.

TABLE 7

| Sample ID | Commercial ELISA | PvEXP1 S/N |
|---|---|---|
| M001 | Pos | 4.17 |
| M002 | Pos | 1.38 |
| M003 | Pos | 2.87 |
| M004 | Pos | 2.35 |
| M005 | Neg | 0.92 |
| M006 | Pos | 2.29 |
| M021 | Neg | 2.08 |
| M022 | Pos | 1.74 |
| M023 | Neg | 1.13 |
| M024 | Neg | 1.15 |
| M025 | Neg | 1.57 |
| M027 | Neg | 1.60 |
| M028 | Neg | 2.97 |
| M029 | Pos | 6.91 |
| M030 | Neg | 1.55 |
| M032 | Neg | 1.75 |
| M033 | Neg | 1.85 |
| M034 | Pos | 1.76 |
| M035 | Pos | 5.69 |
| M036 | Pos | 1.60 |
| M037 | Neg | 1.08 |
| M038 | Pos | 1.10 |
| M039 | Pos | 4.37 |
| M040 | Pos | 17.08 |
| M041 | Pos | 17.98 |
| M042 | Pos | 1.33 |
| M043 | Pos | 57.40 |
| M044 | Pos | 2.13 |
| M045 | Pos | 3.72 |
| M046 | Pos | 1.03 |
| M047 | Pos | 1.65 |
| M048 | Pos | 3.38 |
| M049 | Pos | 1.27 |
| M050 | Pos | 13.51 |
| M060 | Pos | 21.11 |
| M063 | Pos | 1.43 |
| M065 | Pos | 1.38 |
| M080 | Pos | 0.97 |
| M082 | Pos | 1.80 |
| M085 | Pos | 39.26 |
| M093 | Pos | 23.92 |
| M094 | Neg | 1.33 |
| M095 | Neg | 21.62 |
| M101 | Pos | 2.67 |
| M102 | Pos | 45.31 |
| M103 | Pos | 26.20 |
| M104 | Pos | 29.81 |
| M105 | Pos | 4.74 |
| M106 | Pos | 28.46 |
| M107 | Pos | 56.24 |
| M108 | Neg | 6.72 |
| M109 | Pos | 2.41 |
| M110 | Pos | 1.52 |
| M111 | Pos | 2.72 |
| M112 | Neg | 0.53 |
| M113 | Pos | 2.11 |
| M115 | Neg | 0.95 |

TABLE 7-continued

| Sample ID | Commercial ELISA | PvEXP1 S/N |
|---|---|---|
| M119 | Pos | 1.22 |
| M120 | Neg | 0.57 |
| M121 | Pos | 14.43 |
| M122 | Neg | 1.61 |
| M123 | Neg | 0.76 |
| M126 | Neg | 0.67 |
| M135 | Pos | 2.12 |
| M146 | Pos | 48.40 |

A total of 18 samples were reactive with PvEXP1. Samples M095 and M108 were reactive with PvEXP1 but not reactive with the commercial immunoassay.

In Table 8 below, samples were from a population highly endemic for malaria. Twenty-eight of the twenty-nine samples were reactive with the commercial assay, and nineteen of the twenty-nine had S/N values greater than 5.0 in the Prism assay.

TABLE 8

| Sample ID | Commercial ELISA | PvEXP1 S/N |
|---|---|---|
| 647-12 | Pos | 0.66 |
| 427-41 | Pos | 77.54 |
| 1045-36 | Pos | 21.04 |
| ABB/CE/306/00 | Pos | 0.98 |
| 1044-35 | Pos | 54.25 |
| ABB775 | Pos | 28.53 |
| A1795 | Pos | 20.30 |
| 645-10 | Pos | 17.90 |
| 5685-35 | Pos | 20.14 |
| 179-16 | Pos | 19.55 |
| ABB/LT/14/00 | Pos | 3.92 |
| ABB/CE/320/00 | Pos | 5.97 |
| 958-8 | Pos | 6.65 |
| 5621-2 | Neg | 1.27 |
| A1371 | Pos | 4.81 |
| 609-39 | Pos | 10.22 |
| ABB/CE/322/00 | Pos | 12.34 |
| 4098-28 | Pos | 20.29 |
| 240-16 | Pos | 5.75 |
| ABB822 | Pos | 3.13 |
| ABB1041 | Pos | 6.13 |
| ABB/CE/344/00 | Pos | 20.00 |
| 315-15 | Pos | 13.21 |
| 478-24 | Pos | 4.07 |
| 193-15 | Pos | 5.79 |
| 783-51 | Pos | 4.08 |
| 612-2 | Pos | 3.88 |
| ABB/CE/310/00 | Pos | 3.23 |
| 90-12 | Pos | 10.67 |
| ABB866 | Pos | 1.24 |
| K076 | Pos | 3.11 |

One skilled in the art would readily appreciate that the present disclosure is well adapted to carry out the objects and obtain the ends and advantages mentioned, as well as those inherent therein. The molecular complexes and the methods, procedures, treatments, molecules, specific compounds described herein are presently representative of preferred embodiments, are exemplary, and are not intended as limitations on the scope of the invention. It will be readily apparent to one skilled in the art that varying substitutions and modifications can be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably can be practiced in the absence of any element or elements, limitation or limitations which is not specifically disclosed herein. Thus, for example, in each instance herein any of the terms "comprising," "consisting essentially of" and "consisting of" can be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present disclosure has been specifically disclosed by preferred embodiments and optional features, modification and variation of the concepts herein disclosed can be resorted to by those skilled in the art, and that such modifications and variations are considered to be within the scope of this invention as defined by the appended claims.

ADDITIONAL CITATIONS

Ausubel, F. M., R. Brent, R. E. Kingston, et al. 1987. Current protocols in molecular biology. John Wiley & Sons, New York.

Boerner, P., R. Lafond, W. Z. Lu, et al. 1991. Production of antigen-specific human monoclonal antibodies from in vitro-primed human splenocytes. *J Immunol.* 147:86-95.

Brennan, M., P. F. Davison, and H. Paulus. 1985. Preparation of bispecific antibodies by chemical recombination of monoclonal immunoglobulin G1 fragments. *Science.* 229:81-3.

Buchardt, O., P. Nielsen, and R. Berg. 1992. PEPTIDE NUCLEIC ACIDS.

Carter, P. 1986. Site-directed mutagenesis. *Biochem J.* 237:1-7.

Charoenvit, Y., V. F. Majam, G. Corradin, et al. 1999. CD4(+) T-cell- and gamma interferon-dependent protection against murine malaria by immunization with linear synthetic peptides from a *Plasmodium yoelii* 17-kilodalton hepatocyte erythrocyte protein. *Infect Immun.* 67:5604-14.

Doderer, C., A. Heschung, P. Guntz, et al. 2007. A new ELISA kit which uses a combination of *Plasmodium falciparum* extract and recombinant *Plasmodium vivax* antigens as an alternative to IFAT for detection of malaria antibodies. *Malar J.* 6:19.

Elghouzzi, M. H., A. Senegas, T. Steinmetz, et al. 2008. Multicentric evaluation of the DiaMed enzyme-linked immunosorbent assay malaria antibody test for screening of blood donors for malaria. *Vox Sang.* 94:33-40.

Fino, J. U.S. Pat. No. 5,464,746. 1995. HAPTENS, TRACERS, IMMUNOGENS AND ANTIBODIES FOR CARBAZOLE AND DIBENZOFURAN DERIVATIVES.

Fishwild, D. M., S. L. O'Donnell, T. Bengoechea, et al. 1996. High-avidity human IgG kappa monoclonal antibodies from a novel strain of minilocus transgenic mice [see comments]. *Nat Biotechnol.* 14:845-51.

Galfre, G., S. C. Howe, C. Milstein, et al. 1977. Antibodies to major histocompatibility antigens produced by hybrid cell lines. *Nature.* 266:550-2.

Girard, M. P., Z. H. Reed, M. Friede, et al. 2007. A review of human vaccine research and development: malaria. *Vaccine.* 25:1567-80.

Goding, J. W. 1996. Monoclonal antibodies: Principles and Practice. Academic Press, San Diego. 492 pp.

Harlow, E., and D. Lane. 1988. Antibodies: A laboratory manual. Cold Spring Harbor Laboratory Press, Cold Spring Harbor. 726 pp.

Harlow, E., and D. Lane. 1999. Using antibodies: A laboratory manual. Cold Spring Harbor Laboratory PRess, Cold Spring Harbor, N.Y.

Holliger, P., T. Prospero, and G. Winter. 1993. "Diabodies": small bivalent and bispecific antibody fragments. *Proc Natl Acad Sci USA*. 90:6444-8.

Hoogenboom, H. R., A. D. Griffiths, K. S. Johnson, et al. 1991. Multi-subunit proteins on the surface of filamentous phage: methodologies for displaying antibody (Fab) heavy and light chains. *Nucleic Acids Res*. 19:4133-7.

Hope, I. A., R. Hall, D. L. Simmons, et al. 1984. Evidence for immunological cross-reaction between sporozoites and blood stages of a human malaria parasite. *Nature*. 308:191-4.

Jones, J. D., P. Dunsmuir, and J. Bedbrook. 1985. High level expression of introduced chimaeric genes in regenerated transformed plants. *Embo J*. 4:2411-8.

Jones, P. T., P. H. Dear, J. Foote, et al. 1986. Replacing the complementarity-determining regions in a human antibody with those from a mouse. *Nature*. 321:522-5.

Kara, U., B. Murray, C. Pam, et al. 1990. Chemical characterization of the parasitophorous vacuole membrane antigen QF 116 from *Plasmodium falciparum*. *Mol Biochem Parasitol*. 38:19-23.

Kaufman, R. J. 1990. Vectors used for expression in mammalian cells. *Methods Enzymol*. 185:487-511.

Kim, S., H. J. Ahn, T. S. Kim, et al. 2003. ELISA detection of vivax malaria with recombinant multiple stage-specific antigens and its application to survey of residents in endemic areas. *Korean J Parasitol*. 41:203-7.

Kitchen, A. D., P. H. Lowe, K. Lalloo, et al. 2004. Evaluation of a malarial antibody assay for use in the screening of blood and tissue products for clinical use. *Vox Sang*. 87:150-5.

Kostelny, S. A., M. S. Cole, and J. Y. Tso. 1992. Formation of a bispecific antibody by the use of leucine zippers. *J Immunol*. 148:1547-53.

Lee, J. S., W. G. Kho, H. W. Lee, et al. 1998. Current status of vivax malaria among civilians in Korea. *Korean J Parasitol*. 36:241-8.

Lonberg, N., and D. Huszar. 1995. Human antibodies from transgenic mice. *Int Rev Immunol*. 13:65-93.

Lonberg, N., L. D. Taylor, F. A. Harding, et al. 1994. Antigen-specific human antibodies from mice comprising four distinct genetic modifications [see comments]. *Nature*. 368: 856-9.

Luckow, V. A. 1991. Cloning and expression of heterologous genes in insect cells with baculovirus vectors. In Recombinant DNA technology and applications. Vol. A. Prokop, R. K. Bajpai, and C. Ho, editors. McGraw-Hill, New York. 97-152.

Marks, J. D., A. D. Griffiths, M. Malmqvist, et al. 1992. By-passing immunization: building high affinity human antibodies by chain shuffling. *Biotechnology (N Y)*. 10:779-83.

Marks, J. D., H. R. Hoogenboom, T. P. Bonnert, et al. 1991. By-passing immunization. Human antibodies from V-gene libraries displayed on phage. *J Mol Biol*. 222:581-97.

Mattingly, P. U.S. Pat. No. 5,424,414. 1995. HAPTENS, TRACERS, IMMUNOGENS AND ANTIBODIES FOR 3-PHENYL-A-ADAMANTANEACETIC ACIDS.

Meraldi, V., I. Nebie, R. Moret, et al. 2002. Recognition of synthetic polypeptides corresponding to the N- and C-terminal fragments of *Plasmodium falciparum* Exp-1 by T-cells and plasma from human donors from African endemic areas. *Parasite Immunol*. 24:141-50.

Mertens, G., T. Vervoort, S. Heylen, et al. 1999. Malaria antibody ELISA insufficiently sensitive for blood donor screening. *Vox Sang*. 77:237-8.

Milstein, C., and A. C. Cuello. 1983. Hybrid hybridomas and their use in immunohistochemistry. *Nature*. 305:537-40.

Morrison, S. L., L. Wims, S. Wallick, et al. 1987. Genetically engineered antibody molecules and their application. *Ann N Y Acad Sci*. 507:187-98.

Mullis, K., F. Faloona, S. Scharf, et al. 1986. Specific enzymatic amplification of DNA in vitro: the polymerase chain reaction. *Cold Spring Harb Symp Quant Biol*. 51 Pt 1:263-73.

Mungai, M., G. Tegtmeier, M. Chamberland, et al. 2001. Transfusion-transmitted malaria in the United States from 1963 through 1999. *N Engl J Med*. 344:1973-8.

Munson, P. J., and D. Rodbard. 1980. Ligand: a versatile computerized approach for characterization of ligand-binding systems. *Anal Biochem*. 107:220-39.

Nielsen, P. E., M. Egholm, R. H. Berg, et al. 1991. Sequence-selective recognition of DNA by strand displacement with a thymine-substituted polyamide. *Science*. 254:1497-500.

Okamura, J., and R. Goldberg. 1989. Regulation of plant gene expression: general principles. In The Biochemistry of Plants: A Comprehensive Treatise. Vol. 15. P. Stumpf and E. Conn, editors. Academic Press, New York. 1-82.

Reisfeld, R. A., and S. Sell. 1985. Monoclonal antibodies and cancer therapy: Proceedings of the Roche-UCLA symposium held in Park City, Utah, Jan. 26-Feb. 2, 1985. Alan R. Liss, New York. 609 pp.

Riechmann, L., M. Clark, H. Waldmann, et al. 1988. Reshaping human antibodies for therapy. *Nature*. 332:323-7.

Rodrigues, M. H., M. G. Cunha, R. L. Machado, et al. 2003. Serological detection of *Plasmodium vivax* malaria using recombinant proteins corresponding to the 19-kDa C-terminal region of the merozoite surface protein-1. *Malar J*. 2:39.

Ruth, J. U.S. Pat. No. 4,948,882. 1990. Ruth, J. 1990. SINGLE-STRANDED LABELED OLIGONUCLEOTIDES, REACTIVE MONOMERS AND METHODS OF SYNTHESIS.

Sambrook, J. 1989. Molecular cloning: a laboratory manual. Cold Spring Harbor Laboratory, Cold Spring Harbor.

Schade, R., C. Staak, C. Hendriksen, et al. 1996. The production of avian (egg yold) antibodies: IgY. The report and recommendations of ECVAM workshop. *Alternatives to Laboratory Animals (ATLA)*. 24:925-934.

Schnieke, A. E., A. J. Kind, W. A. Ritchie, et al. 1997. Human factor IX transgenic sheep produced by transfer of nuclei from transfected fetal fibroblasts. *Science*. 278:2130-3.

Seed, C. R., A. Cheng, T. M. Davis, et al. 2005. The efficacy of a malarial antibody enzyme immunoassay for establishing the reinstatement status of blood donors potentially exposed to malaria. *Vox Sang*. 88:98-106.

Shalaby, M. R., H. M. Shepard, L. Presta, et al. 1992. Development of humanized bispecific antibodies reactive with cytotoxic lymphocytes and tumor cells overexpressing the HER2 protooncogene. *J Exp Med*. 175:217-25.

She, R. C., M. L. Rawlins, R. Mohl, et al. 2007. Comparison of immunofluorescence antibody testing and two enzyme immunoassays in the serologic diagnosis of malaria. *J Travel Med*. 14:105-11.

Sherman, I. W. 1985. Membrane structure and function of malaria parasites and the infected erythrocyte. *Parasitology*. 91 (Pt 3):609-45.

Simmons, D., G. Woollett, M. Bergin-Cartwright, et al. 1987. A malaria protein exported into a new compartment within the host erythrocyte. *Embo J.* 6:485-91.

Son, E. S., T. S. Kim, and H. W. Nam. 2001. Western blot diagnosis of vivax malaria with multiple stage-specific antigens of the parasite. *Korean J Parasitol.* 39:171-6.

Srivastava, I. K., M. Schmidt, M. Grall, et al. 1991. Comparative evaluation of an ELISA based on recombinant polypeptides and IFA for serology of malaria. *J Trop Med Hyg.* 94:189-94.

Suresh, M. R., A. C. Cuello, and C. Milstein. 1986. Bispecific monoclonal antibodies from hybrid hybridomas. *Methods Enzymol.* 121:210-28.

Tolle, R., K. Fruh, O. Doumbo, et al. 1993. A prospective study of the association between the human humoral immune response to *Plasmodium falciparum* blood stage antigen gp190 and control of malarial infections. *Infect Immun.* 61:40-7.

Traunecker, A., F. Oliveri, and K. Karjalainen. 1991. Myeloma based expression system for production of large mammalian proteins. *Trends Biotechnol.* 9:109-13.

Turner, R., and G. D. Foster. 1995. The potential exploitation of plant viral translational enhancers in biotechnology for increased gene expression. *Mol Biotechnol.* 3:225-36.

Urlaub, G., and L. A. Chasin. 1980. Isolation of Chinese hamster cell mutants deficient in dihydrofolate reductase activity. *Proc Natl Acad Sci USA.* 77:4216-20.

van der Krol, A. R., J. N. Mol, and A. R. Stuitje. 1988. Modulation of eukaryotic gene expression by complementary RNA or DNA sequences. *Biotechniques.* 6:958-76.

Verhoeyen, M., C. Milstein, and G. Winter. 1988. Reshaping human antibodies: grafting an antilysozyme activity. *Science.* 239:1534-6.

Vinetz, J. M., J. Li, T. F. McCutchan, et al. 1998. *Plasmodium malariae* infection in an asymptomatic 74-year-old Greek woman with splenomegaly. *N Engl J Med.* 338:367-71.

Wells, J. A., M. Vasser, and D. B. Powers. 1985. Cassette mutagenesis: an efficient method for generation of multiple mutations at defined sites. *Gene.* 34:315-23.

Wild, D. 2001. The Immunoassay handbook. Nature Pub. Group, London. xxix, 906 p. pp.

Wyler, D. 1992. *Plasmodium* and Babeis. In Infectious diseases. Vol. S. L. Gorbach, J. G. Bartlett, and N. R. Blacklow, editors. Saunders, Philadelphia. 407.

Zoller, M. J., and M. Smith. 1987. Oligonucleotide-directed mutagenesis: a simple method using two oligonucleotide primers and a single-stranded DNA template. *Methods Enzymol.* 154:329-50.

Zon, G. 1988. Oligonucleotide analogues as potential chemotherapeutic agents. *Pharm Res.* 5:539-49.

---

What is claimed is:

1. A purified protein encoded by a nucleic acid, wherein said nucleic acid comprises a nucleotide sequence encoding a polypeptide, wherein the amino acid sequence of said polypeptide has at least 70% identity to an amino acid sequence selected from the group consisting of SEQ ID NO:2, SEQ ID NO:3 and amino acids 2-50 of SEQ ID NO:2.

2. A purified protein comprising an amino acid sequence having at least 70% identity to an amino acid sequence selected from the group consisting of SEQ ID NO:2, SEQ ID NO:3, and amino acids 2-50 of SEQ ID NO:2.

3. A kit for determining the presence of antibody to *P. vivax* in a test sample comprising: (a) an antigen comprising an amino acid sequence selected from the group consisting of SEQ ID NO:2, SEQ ID NO:3, and amino acids 2-50 of SEQ ID NO:2; and (b) a conjugate comprising an antibody attached to a signal-generating compound capable of generating a detectable signal.

4. A kit for determining the presence of antibody to *P. malariae, P. ovale, P. vivax* and *P. falciparum* in a test sample comprising:

(a) an antigen comprising an amino acid sequence selected from the group consisting of SEQ ID NO:2, SEQ ID NO:3, and amino acids 2-50 of SEQ ID NO:2, a *P. ovale*, a *P. malariae* antigen and a *P. falciparum* antigen; and (b) a conjugate comprising an antibody attached to a signal generating compound capable of generating a detectable signal.

5. A kit for detecting antibodies to *P. malariae, P. ovale, P. vivax* and *P. falciparum* in a test sample comprising:

(a) an anti-antibody; and (b) an antigen comprising an amino acid sequence selected from the group consisting of SEQ ID NO:2, SEQ ID NO:3, and amino acids 2-50 of SEQ ID NO:2, a *P. ovale* antigen, a *P. malariae* antigen and a *P. falciparum* antigen.

6. A kit for detecting antibodies to *P. malariae, P. ovale, P. vivax* and *P. falciparum* in a test sample comprising:

(a) an anti-antibody and (b) a first conjugate comprising an antigen comprising an amino acid sequence selected from the group consisting of SEQ ID NO:2, SEQ ID NO:3, and amino acids 2-50 of SEQ ID NO:2, attached to a signal generating compound capable of generating a detectable signal, a second conjugate comprising a *P. ovale* antigen; a third conjugate comprising a *P. malariae* antigen attached to a signal generating compound capable of generating a detectable signal and a fourth conjugate comprising a *P. falciparum* antigen attached to a signal generating compound capable of generating a detectable signal.

7. A method of detecting antibodies to *P. vivax* in a test sample suspected of containing the antibodies comprising the steps of (a) contacting the test sample with an antigen comprising an amino acid sequence selected from the group consisting of SEQ ID NO:2, SEQ ID NO:3, and amino acids 2-50 of SEQ ID NO:2, for a time and under conditions sufficient for the formation of antibody/antigen complexes; and (b) detecting the presence of antibodies present in the test sample by detecting presence of the antibody/antigen complexes.

8. A method of detecting antibodies to *P. vivax* in a test sample suspected of containing the antibodies comprising the steps of:
   (a) contacting the test sample with an antigen comprising an amino acid sequence selected from the group consisting of SEQ ID NO:2, SEQ ID NO:3, and amino acids 2-50 of SEQ ID NO:2, for a time and under conditions sufficient to allow for the formation of antibody/antigen complexes;
   (b) adding a conjugate to resulting antibody/antigen complexes for a time and under conditions sufficient to allow the conjugate to bind to bound antibody, wherein the conjugate comprises an antibody attached to a signal generating compound capable of generating a detectable signal; and
   (c) detecting the presence of antibodies present in the test sample by detecting presence of the signal generated by the signal generating compound.

9. A method of detecting antibodies to *P. vivax* in a test sample suspected of containing the antibodies comprising the steps of:
   (a) contacting the test sample with an antigen comprising an amino acid sequence selected from the group consisting of SEQ ID NO:2, SEQ ID NO:3, and amino acids 2-50 of SEQ ID NO:2, for a time and under conditions sufficient to allow for the formation of antibody/antigen complexes;
   (b) adding a conjugate to resulting antibody/antigen complexes for a time and under conditions sufficient to allow the conjugate to bind to bound antibody, wherein the conjugate comprises an antigen comprising an amino acid sequence selected from the group consisting of SEQ ID NO:2, SEQ ID NO:3, and amino acids 2-50 of SEQ ID NO:2, attached to a signal generating compound capable of generating a detectable signal; and
   (c) detecting the presence of antibodies present in the test sample by detecting presence of the signal generated by the signal generating compound.

10. A method of detecting the presence of *P. vivax* antibodies in a test sample suspecting of containing the antibodies comprising the steps of:
    (a) contacting the test sample with anti-antibody for a time and under conditions sufficient to allow for formation of anti-antibody/*P. vivax* antibody complexes;
    (b) adding antigen to the resulting anti-antibody/*P. vivax* antibody complexes for a time and under conditions sufficient to allow the antigen to bind to bound antibody, wherein the antigen comprises an amino acid sequence selected from the group consisting of SEQ ID NO:2, SEQ ID NO:3, and amino acids 2-50 of SEQ ID NO:2;
    (c) adding a conjugate to the resulting anti-antibody/*P. vivax* antibody/antigen complexes, wherein the conjugate comprises a composition comprising a monoclonal or polyclonal antibody attached to a signal generating compound capable of generating a detectable signal; and
    (d) detecting presence of antibodies which can be present in the test sample by detecting presence of the signal generated by the signal generating compound.

11. A method of detecting antibodies to *P. malariae, P. falciparum, P. vivax* and *P. ovale* in a test sample suspected of containing at least one of the antibodies comprising the steps of:
    (a) contacting the test sample with: (i) an antigen comprising an amino acid sequence selected from the group consisting of SEQ ID NO:2, SEQ ID NO:3, and amino acids 2-50 of SEQ ID NO:2, (ii) an antigen from *P. falciparum*; (iii) an antigen from *P. ovale*, and (iv) an antigen from *P. malariae*, for a time and under conditions sufficient for the formation of *P. malariae* antibody/antigen complexes, *P. falciparum* antibody/antigen complexes, *P. vivax* antibody/antigen complexes and *P. ovale* antibody/antigen complexes; and
    (b) detecting the presence of antibodies present in the test sample by detecting presence of one or more of the complexes.

12. A method of detecting antibodies to *P. malariae, P. ovale, P. vivax* and *P. falciparum* in a test sample suspected of containing at least one of the antibodies comprising the steps of:
    (a) contacting the test sample with: (i) an antigen comprising an amino acid sequence selected from the group consisting of SEQ ID NO:2, SEQ ID NO:3, and amino acids 2-50 of SEQ ID NO:2, (ii) a *P. ovale* antigen, (iii) a *P. malariae* antigen and (iv) a *P. falciparum* antigen, for a time and under conditions sufficient to allow for the formation of *P. malariae* antibody/antigen complexes, *P. ovale* antibody/antigen complexes, *P. vivax* antibody/antigen complexes and *P. falciparum* antibody/antigen complexes;
    (b) adding four conjugates to the resulting antibody/antigen complexes for a time and under conditions sufficient to allow each conjugate to bind to bound antibody, wherein a first conjugate comprises an antigen comprising an amino acid sequence selected from the group consisting of SEQ ID NO:2, SEQ ID NO:3, and amino acids 2-50 of SEQ ID NO:2, attached to a signal generating compound capable of generating a detectable signal; a second conjugate comprises if *P. ovale* antigen attached to a signal generating signal capable of generating a detectable signal; a third conjugate comprises a *P. malariae* antigen attached to a signal generating signal capable of generating a detectable signal and a fourth conjugate comprises a *P. falciparum* antigen attached to a signal generating compound capable of generating a detectable signal; and
    (c) detecting the presence of antibody to *P. malariae, P. ovale, P. vivax* and *P. falciparum* which can be present in the test sample by detecting presence of the signal generated by the signal generating compound.

13. A method of detecting antibodies to *P. malariae, P. ovale, P. vivax* and *P. falciparum* in a test sample suspected of containing at least one of the antibodies comprising the steps of:
    (a) contacting the test sample with (i) an antigen comprising an amino acid sequence selected from the group consisting of SEQ ID NO:2, SEQ ID NO:3, and amino acids 2-50 of SEQ ID NO:2, (ii) *P. malariae* antigen, (iii) a *P. vivax* antigen and (iv) a *P. falciparum* antigen, for a time and under conditions sufficient to allow for the formation of *P. malariae* antibody/antigen complexes, *P. ovale* antibody/antigen complexes, *P. vivax* antibody/antigen complexes and *P. falciparum* antibody/antigen complexes;
    (b) adding a conjugate to the resulting antibody/antigen complexes for a time and under conditions sufficient to allow each conjugate to bind to bound antibody, wherein the conjugate comprises an antibody attached to a signal generating compound capable of generating a detectable signal; and
    (c) detecting the presence of antibody to *P. malariae, P. ovale, P. vivax* and *P. falciparum* antibody which can be present in the test sample by detecting presence of the signal generated by the signal generating compound.

14. A method for detecting the presence of antibodies to *P. malariae, P. ovale, P. vivax* and *P. falciparum* in a test sample suspected of containing at least one of the antibodies comprising the steps of:
(a) contacting the test sample with anti-antibody for a time and under conditions sufficient to allow for formation of anti-antibody/*P. vivax*, anti-antibody/*P. malariae*, anti-antibody/*P. ovale*, and anti-antibody/*P. falciparum* complexes;
(b) adding a first antigen, a second antigen, a third antigen, and a fourth antigen to the resulting anti-antibody/*P. vivax*, anti-antibody/*P. malariae*, anti-antibody/*P. ovale*, and anti-antibody/*P. falciparum* complexes for a time and under conditions sufficient to allow the antigens to bind to bound antibody, wherein (i) the first antigen comprises an amino acid sequence selected from the group consisting of SEQ ID NO:2, SEQ ID NO:3, and amino acids 2-50 of SEQ ID NO:2; (ii) the second antigen comprises a *P. ovale* antigen; (iii) the third antigen comprises a *P. malariae* antigen; and (iv) the fourth antigen comprises a *P. falciparum* antigen;
(c) adding a first conjugate, a second conjugate, a third conjugate and a fourth conjugate to the resulting anti-antibody/antibody/antigen complexes for a time and under conditions sufficient to allow the conjugates to bind to bound antibody, wherein the conjugates are each attached to a signal generating compound capable of generating a detectable signal; and (i) the first conjugate comprises a composition comprising a monoclonal or polyclonal antibody raised against *P. vivax* antibody/antigen complexes;
(ii) the second conjugate comprises a composition comprising a monoclonal or polyclonal antibody raised against *P. ovale* antibody/antigen complexes; (iii) the third conjugate comprises a composition comprising a monoclonal or polyclonal antibody raised against *P. malariae* antibody/antigen complexes; (vi) the fourth conjugate comprises a composition comprising a monoclonal or polyclonal antibody raised against *P. falciparum* antibody/antigen complexes; and
(d) detecting presence of antibodies which can be present in the test sample by detecting presence of the signal generated by the signal generating compounds.

15. A method for detecting the presence of antibodies to *P. malariae, P. ovale, P. vivax* and *P. falciparum* in a test sample suspected of containing at least one of the antibodies comprising the steps of
(a) contacting the test sample with anti-antibody to allow for the formation of anti-antibody/antibody complexes;
(b) adding a first conjugate, a second conjugate, a third conjugate and a fourth conjugate to resulting anti-antibody/antibody complexes for a time and under conditions sufficient to allow the conjugates to bind to bound antibody, wherein the first conjugate comprises an antigen comprising an amino acid sequence selected from the group consisting of SEQ ID NO:2, SEQ ID NO:3, and amino acids 2-50 of SEQ ID NO:2, attached to a signal generating compound capable of generating a detectable signal, wherein the second conjugate comprises a *P. ovale* antigen attached to a signal generating compound capable of generating a detectable signal, wherein the third conjugate comprises a *P. vivax* antigen attached to a signal generating compound capable of generating a detectable signal, and wherein the fourth conjugate comprises a *P. falciparum* antigen attached to a signal generating compound capable of generating a detectable signal; and
(c) detecting the presence of antibodies to *P. malariae, P. ovate, P. vivax* and *P. falciparum* in the test sample by detecting presence of the signal generated by the signal generating compound.

16. A method of detecting the presence of *P. vivax* antibodies in a test sample suspected of containing the antibodies comprising the steps of
(a) contacting the test sample with anti-antibody for a time and under conditions sufficient to allow for formation of anti-antibody/*P. vivax* antibody complexes;
(b) adding antigen to the resulting anti-antibody/*P. vivax* antibody complexes for a time and under conditions sufficient to allow the antigen to bind to bound antibody, wherein the antigen comprises an amino acid sequence selected from the group consisting of SEQ ID NO:2, SEQ ID NO:3, and amino acids 2-50 of SEQ ID NO:2, wherein the antigen is conjugated to a signal generating compound capable of generating a detectable signal; and
(c) detecting presence of antibodies which can be present in the test sample by detecting presence of the signal generated by the signal generating compound.

* * * * *

UNITED STATES PATENT AND TRADEMARK OFFICE
CERTIFICATE OF CORRECTION

PATENT NO.         : 8,318,897 B2                          Page 1 of 1
APPLICATION NO.    : 13/219802
DATED              : November 27, 2012
INVENTOR(S)        : Larry G. Birkenmeyer et al.

It is certified that error appears in the above-identified patent and that said Letters Patent is hereby corrected as shown below:

In the Claims

Column 50, claim 12,
Line 34, "a second conjugate comprises if *P. ovale* antigen" should read –
"a second conjugate comprises a *P. ovale* antigen"

Signed and Sealed this
Third Day of June, 2014

Michelle K. Lee
*Deputy Director of the United States Patent and Trademark Office*